United States Patent
Sowadski

(10) Patent No.: US 11,230,741 B2
(45) Date of Patent: Jan. 25, 2022

(54) METHODS AND SYSTEMS FOR DETERMINATION OF AN EFFECTIVE THERAPEUTIC REGIMEN AND DRUG DISCOVERY

(71) Applicant: DNA-SEQ, INC., La Jolla, CA (US)

(72) Inventor: Janusz Sowadski, La Jolla, CA (US)

(73) Assignee: DNA-SEQ, Inc., La Jolla, CA (US)

( * ) Notice: Subject to any disclaimer, the term of this patent is extended or adjusted under 35 U.S.C. 154(b) by 0 days.

(21) Appl. No.: 16/551,541

(22) Filed: Aug. 26, 2019

(65) Prior Publication Data

US 2020/0208222 A1 Jul. 2, 2020

Related U.S. Application Data

(63) Continuation of application No. 15/346,671, filed on Nov. 8, 2016, now Pat. No. 10,392,669, which is a continuation-in-part of application No. 14/606,918, filed on Jan. 27, 2015, now Pat. No. 10,093,982.

(60) Provisional application No. 61/932,156, filed on Jan. 27, 2014.

(51) Int. Cl.

| | |
|---|---|
| *C12Q 1/6886* | (2018.01) |
| *G16B 15/00* | (2019.01) |
| *G16C 20/30* | (2019.01) |
| *G16B 15/30* | (2019.01) |
| *C40B 30/04* | (2006.01) |
| *G16B 30/00* | (2019.01) |
| *G16B 40/00* | (2019.01) |
| *G16B 50/00* | (2019.01) |
| *G16B 50/30* | (2019.01) |
| *G16B 30/10* | (2019.01) |
| *G16B 50/10* | (2019.01) |
| *G16B 40/20* | (2019.01) |

(52) U.S. Cl.
CPC .......... *C12Q 1/6886* (2013.01); *G16B 15/00* (2019.02); *G16B 15/30* (2019.02); *G16B 30/00* (2019.02); *G16B 30/10* (2019.02); *G16B 40/00* (2019.02); *G16B 40/20* (2019.02); *G16B 50/00* (2019.02); *G16B 50/10* (2019.02); *G16B 50/30* (2019.02); *G16C 20/30* (2019.02); *C12Q 2600/106* (2013.01); *C12Q 2600/118* (2013.01); *C12Q 2600/136* (2013.01); *C12Q 2600/156* (2013.01); *C40B 30/04* (2013.01)

(58) Field of Classification Search
None
See application file for complete search history.

(56) References Cited

U.S. PATENT DOCUMENTS

2005/0164300 A1 7/2005 Artis et al.
2008/0268068 A1 10/2008 Tai

FOREIGN PATENT DOCUMENTS

WO WO-2013056178 A2 * 4/2013 .......... A61K 31/565
WO WO 2013056178 A2 4/2013

OTHER PUBLICATIONS

Nettles et al., "NFkappaB selectivity of estrogen receptor ligands revealed by comparative crystallographic analyses," Nat. Chem. Biol. 2008, 4(4):241-247. (Year: 2008).*
Allen et al., "Identification and Characterization of Mutations in Hepatitis B Virus Resistant to Lamivudine"; Hepatology, 1998, vol. 27, No. 6, pp. 1670-1677, (XP055391994).
Betel et al., "Kangaroo—A pattern-matching program for biological sequences"; BMC Bioinformatics, 2002, vol. 3, No. 1, p. 20, (XP021013549).
Hou et al., "Predicting drug resistance of the HIV-1 protease using molecular interaction energy components," Proteins 2009, 74:837-846. (Year: 2009).
International Search Report dated May 6, 2015 regarding PCT/US2015/013133.
Nettles et al., "NFKB selectivity of estrogen receptor ligands revealed by comparative crystallographic analyses"; Nature Chemical Biology, 2008, vol. 4, No. 4, pp. 241-247.
Roskoski et al., "Structure and regulation of Kit protein-tyrosine kinase—The stem cell factor receptor" Biochemical and Biophysical Research Communications, Oct. 4, 2005, vol. 338, p. 1307-1315.
Supplementary Partial European Search Report dated Aug. 1, 2017 regarding EP 15 739 850.4.
Tarn et al., "Analysis of KIT Mutations in Sporadic and Familial Gastrointestinal Stromal Tumors: Therapeutic Implications through Protein Modeling," Clin. Cancer Res. 2005, 11:3668-3677. (Year: 2005).

* cited by examiner

*Primary Examiner* — Kaijiang Zhang
(74) *Attorney, Agent, or Firm* — DLA Piper LLP (US)

(57) ABSTRACT

The present invention relates to the discovery of a method for identifying a treatment regimen for a patient diagnosed with cancer, predicting patient resistance to therapeutic agents and identifying new therapeutic agents. Specifically, the present invention relates to the use of an algorithm to identify a mutation in a kinase, determine if the mutation is an activation or resistance mutation and then to suggest an appropriate therapeutic regimen. The invention also relates to the use of a pattern matching algorithm and a crystal structure library to predict the functionality of a gene mutation, predict the specificity of small molecule kinase inhibitors and for the identification of new therapeutic agents.

11 Claims, 18 Drawing Sheets

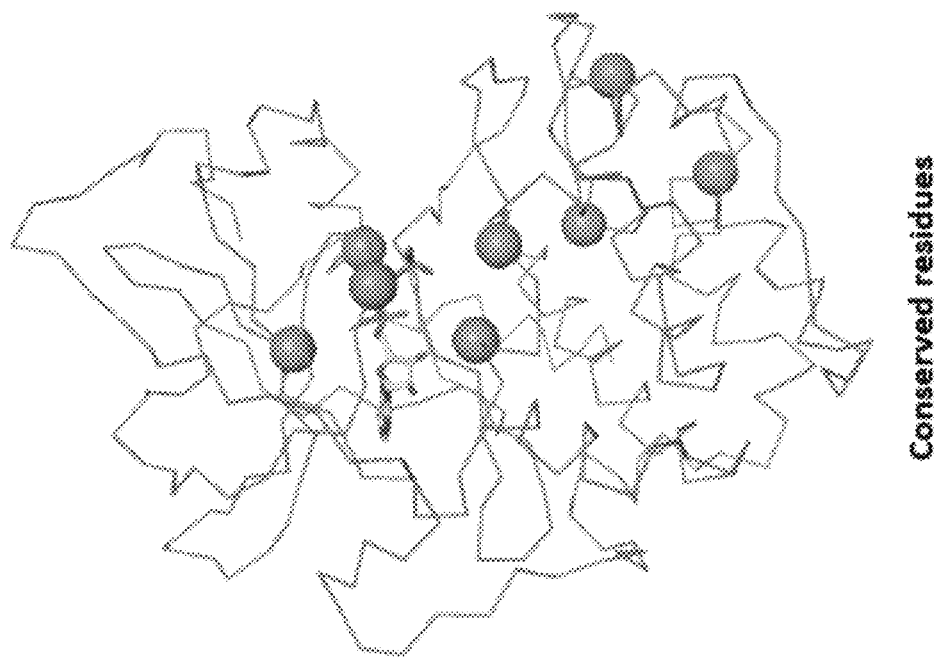
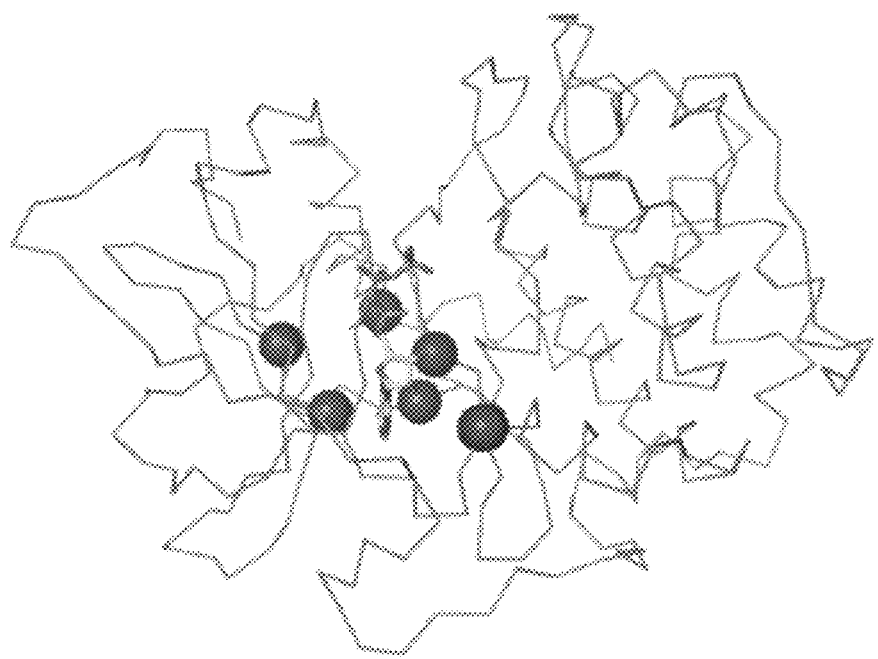

METHODS AND SYSTEMS FOR DETERMINATION OF AN EFFECTIVE THERAPEUTIC REGIMEN AND DRUG DISCOVERY

CROSS-REFERENCE TO RELATED APPLICATIONS

This application is a continuation application of U.S. application Ser. No. 15/346,671 filed Nov. 8, 2016, now issued as U.S. Pat. No. 10,392,669; which is a continuation-in-part application of U.S. application Ser. No. 14/606,918 filed Jan. 27, 2015, now issued as U.S. Pat. No. 10,093,982, which claims the benefit under 35 USC § 119(e) to U.S. Application Ser. No. 61/932,156 filed Jan. 27, 2014, now expired. The disclosure of each of the prior applications is considered part of and is incorporated by reference in the disclosure of this application.

BACKGROUND OF THE INVENTION

Field of the Invention

The invention is directed generally to the prediction of the functionality associated with a gene mutation to identify appropriate therapeutic regimens based on known drugs and the development of novel therapeutics.

Background Information

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers, or malignant tumors, metastasize and grow rapidly in an uncontrolled manner, making timely detection and treatment extremely difficult.

Depending on the cancer type, patients typically have several treatment options available to them including chemotherapy, radiation and antibody-based drugs. Patients frequently develop resistance to one or more cancer treatments. Frequently this resistance is associated with a mutation in the tumor. There currently are no methods available to predict or monitor patients for the development of resistance to cancer treatments.

Complicating the treatment of cancer is the long timeline for the development of new chemotherapeutic agents. The current methodology of small molecule drug discovery is risky due to the lone and expensive development and clinical trial process that occurs prior to validation of the drug in patients. Additionally, the attrition rate for these drugs is high because determination of the drug candidate's efficacy occurs late in the development process after massive expenditures have already occurred. The accumulated costs of the 4-6 years of pre-clinical and Phase 1 clinical trials are large and highly risky for the drug owner.

Thus, there is a need for more effective means for determining which patients will respond to specific cancer therapeutics, to predict which patients will develop resistance to cancer therapeutics and for incorporating such determinations into more effective treatment regimens for patients with anti-cancer therapies. Additionally, there is a need for better methods of quickly predicting which small molecules will be clinically beneficial prior to the need for expensive clinical trials.

Described herein is the use of a proprietary crystal structure library and a unique pattern matching algorithm to predict the functionality of a gene mutation, predict the specificity of a small molecule kinase inhibitor and to streamline drug development by the prediction of virtual molecules to inhibit kinases, for example by identifying previously unknown intermediate states of kinase catalytic cores resulting from activating cancer mutations. This predictive algorithm has been used to select appropriate therapeutic agents to target specific mutations as well as predict or monitor the development of resistance to therapeutic agents based in specific mutations. Further, the predictive algorithm methodology enables the rapid design of new drug candidates based on the specificity profile for the predicted functionality of a mutation.

SUMMARY OF THE INVENTION

The present invention relates to the seminal discovery of a method for identifying a treatment regimen for a patient diagnosed with cancer, predicting patient resistance to therapeutic agents and identifying new therapeutic agents. Specifically, the present invention relates to the use of an algorithm to identify a mutation in a kinase, determine if the mutation is an activation or resistance mutation and then to suggest an appropriate therapeutic regimen. The invention also relates to the use of a pattern matching algorithm and a crystal structure library to predict the functionality of a gene mutation, predict the specificity of small molecule kinase inhibitors and for the identification of new therapeutic agents.

In one embodiment, the present invention provides a method for identifying a therapeutic regimen or predicting resistance to a therapeutic regimen for a patient with cancer comprising obtaining a biologic sample from the patient; identifying a at least one mutation in a gene sequence from the sample; using a pattern matching algorithm to determine if the at least one mutation is an activation mutation or a resistance mutation; and using the pattern matching algorithm and a crystal structure library to identify therapeutic agents to target the activating mutation or for which the patient is resistant; thereby identifying a therapeutic regimen or predicting resistance to a therapeutic regimen. In one aspect, the biological sample is blood, saliva, urine, bone marrow, serum, lymph, cerebrospinal fluid, sputum, stool, organ tissue or ejaculate sample. In an aspect, the at least one mutation is identified by sequence analysis. In one aspect, the at least one mutation is in the gene sequence of a receptor or a kinase. In another aspect, the receptor is an estrogen receptor. In a further aspect, the estrogen receptor is ESR1 or ESR2. In another aspect, the at least one mutation is in the catalytic domain of a kinase. In an additional aspect, the at least one mutation results in a novel kinase conformation. In a specific aspect, the at least one mutation is in the DFG domain. In a further aspect, the crystal structure library comprises a protein crystal structure database and a therapeutic agent crystal structure database. In an additional aspect, the algorithm is subjected to machine learning. In one aspect, the at least one mutation comprises an activation mutation or a resistance mutation. In another aspect, the at least one mutation comprises a mutation in a kinase or a receptor. In certain aspects, the receptor is an estrogen receptor 1 (ESR1) or an estrogen receptor 2 (ESR2). In another aspect, the therapeutic regimen comprises a kinase inhibitor and/or a chemotherapeutic agent. In another aspect, the method further comprises using a three dimensional template to identify therapeutic agents.

In one embodiment, the present invention relates to a method of determining risk for developing resistance or the development of resistance to a therapeutic regimen in an ER+ breast cancer patient comprising obtaining a biological sample and a tumor sample from the patient; contacting each sample with a probe that binds to a sequence in a gene associated with kinase phosphorylation; and comparing the binding of the probe in the biological sample with the binding of the probe in the tumor sample wherein binding of the probe with the biological sample but not the tumor sample is indicative of a tumor that is at risk for developing resistance to a therapeutic regimen. In one aspect, the sample is obtained from the patient following a course of therapy and wherein the course of therapy is ongoing for at least about 1 month to 6 months at the time the sample is obtained. In another aspect, the sample is obtained at intervals throughout the course of therapy. In one aspect, the subject is a human. In a further aspect, the biological sample is blood, saliva, urine, bone marrow, serum, lymph, cerebrospinal fluid, sputum, stool, organ tissue or ejaculate sample. In an additional aspect, the probe detects a mutation in the gene sequence. In a specific aspect, the mutation is a point mutation. In another aspect, the biological sample is a tumor sample and specifically, the tumor sample is a liquid biopsy or a sample of circulating tumor cells (CTCs).

In another aspect, the probe detects a deletion in the gene sequence. In one aspect, the deletion is about 2 to 12 amino acids. In a further aspect, the probe detects a deletion and a single point mutation in the gene sequence. In one aspect probe is at least about 1000 nucleotides, from about 300 to 500 nucleotides or at least about 150 nucleotides for more than one region of the gene sequence. In further aspect, the gene sequence is an ESR receptor gene sequence. In a specific aspect, the ESR receptor is ESR1 or ESR2. In certain aspects, the ESR1 receptor has a point mutation at Y537, E380, L536, and/or D538. In specific aspects the ESR1 mutation is Y537S, Y537A, Y537E or Y537K. In another aspect, the ESR2 receptor has a point mutation at V497 and specifically, the mutation is V497M.

In a further aspect, the therapeutic regimen is treatment with an aromatase inhibitor. In a specific aspect, the therapeutic regimen is treatment with a tamoxifene, Raloxifene and/or a competitor of estrogen in its ER binding site.

In another aspect, the method further comprises predicting a second form of therapy. In certain aspects, the second form of therapy is provided to the patient prior to completion of a therapeutic regimen with a first form of therapy. In another aspect, the first form of therapy is an aromatase inhibitor and the second form of therapy is a non-aromatase inhibitor chemotherapeutic drug. In an additional aspect, the non-aromatase inhibitor chemotherapeutic drug may be antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine, antibodies such as trastuzumab; bevacizumab, OSI-774, Vitaxin; alkaloids, including, microtubule inhibitors (e.g., Vincristine, Vinblastine, and Vindesine, etc.), microtubule stabilizers (e.g., Paclitaxel (Taxol), and Docetaxel, Taxotere, etc.), and chromatin function inhibitors, including, topoisomerase inhibitors, such as, epipodophylloxins (e.g., Etoposide (VP-16), and Teniposide (VM-26), etc.), agents that target topoisomerase I (e.g., Camptothecin and Isirinotecan (CPT-11), etc.); covalent DNA-binding agents (alkylating agents), including, nitrogen mustards (e.g., Mechlorethamine, Chlorambucil, Cyclophosphamide, Ifosphamide, and Busulfan (Myleran), etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); noncovalent DNA-binding agents (antitumor antibiotics), including, nucleic acid inhibitors (e.g., Dactinomycin (Actinomycin D)), anthracyclines (e.g., Daunorubicin (Daunomycin, and Cerubidine), Doxorubicin (Adriamycin), and Idarubicin (Idamycin)), anthracenediones (e.g., anthracycline analogues, such as, (Mitoxantrone)), bleomycins (Blenoxane), etc., and plicamycin (Mithramycin); antimetabolites, including, antifolates (e.g., Methotrexate, Folex, and Mexate), purine antimetabolites (e.g., 6-Mercaptopurine (6-MP, Purinethol), 6-Thioguanine (6-TG), Azathioprine, Acyclovir, Ganciclovir, Chlorodeoxyadenosine, 2-Chlorodeoxyadenosine (CdA), and 2'-Deoxycoformycin (Pentostatin), etc.), pyrimidine antagonists (e.g., fluoropyrimidines (e.g., 5-fluorouracil (Adrucil), 5-fluorodeoxyuridine (FdUrd) (Floxuridine)) etc.), and cytosine arabinosides (e.g., Cytosar (ara-C) and Fludarabine); enzymes, including, L-asparaginase; hormones, including, glucocorticoids, such as, antiestrogens (e.g., Tamoxifen, etc.), nonsteroidal antiandrogens (e.g., Flutamide); platinum compounds (e.g., Cisplatin and Carboplatin); monoclonal antibodies conjugated with anticancer drugs, toxins, and/or radionuclides, etc.; biological response modifiers (e.g., interferons (e.g., IFN-alpha.) and interleukins (e.g., IL-2).

In one aspect, the determination is performed on a computer. In another aspect, the gene sequence is in a database. In a certain aspect, the database contains sequences for the catalytic cores of protein kinases.

In a further embodiment, the present invention provides a method for identifying a drug candidate comprising identifying a mutation for resistance to a first drug by genomic and/or three-dimensional crystallographic analysis; and determining a second drug based on the mutation for resistance due to the first drug, by searching a crystal structure library database to identify a scaffold for a drug candidate as the second drug, thereby identifying a drug candidate. In one aspect, a pattern matching algorithm is used to search the crystal structure library.

In another embodiment, the present invention provides a method for predicting the specificity profile of a therapeutic agent comprising obtaining the crystal structure of the therapeutic agent; and using a pattern matching algorithm to identify targets of the therapeutic agent using a crystal structure library, thereby, predicting the specificity profile of a therapeutic agent. In one aspect, the crystal structure library comprises a protein crystal structure database. In another aspect, the protein crystal structure database comprises the crystal structure of kinases and receptors. In an aspect, the therapeutic agent is a kinase inhibitor. In one aspect, the kinase inhibitor is Afatinib, Axitinib, Bevacizumab, Bosutinib, Cetuximab, Crizotinib, Dasatinib, Erlotinib, Fostamatinib, Gefitinib, Ibrutinib, Imatinib, Lapatinib, Lenvatinib, Masitinib, Mubritinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib or Vemurafenib or a combination thereof. In another aspect, the therapeutic agent is a chemotherapeutic agent. In an additional aspect, the target is a kinase or a receptor. In one aspect, the target is a mutation in a gene sequence. In a further aspect, the gene mutation is in a kinase or a receptor. In certain aspects, the target is the catalytic domain of a kinase. In a specific aspect, the target is the DFG domain. In one aspect, the receptor is an estrogen receptor. In an additional aspect, the specificity profile is used in the selection of a treatment regimen for a patient in need thereof.

In a further embodiment, the present invention provides a method of treating a patient in need thereof comprising obtaining a biologic sample; identifying at least one mutation in a gene from the biologic sample; using a pattern matching algorithm and a crystal structure library to identify at least one therapeutic agent to target the at least one mutation; and administering the identified therapeutic agent to the patient, thereby treating the patient. In one aspect, the patient is diagnosed with cancer. In another aspect, at least 2 gene mutations are identified. In certain aspects, 2, 3, 4, 5, 6, 7, 8, 9, or 10 gene mutations are identified. In a further aspect, the gene mutations are identified by sequence analysis. In an aspect, the crystal structure library comprises the crystal structure of kinases, receptors and ligands. In one aspect, the target is a kinase or a receptor. In an additional aspect, more than one therapeutic agent is selected for the treatment regimen. In a further aspect the at least one chemotherapeutic agent. In certain aspects, one chemotherapeutic agent is a kinase inhibitor. In another aspect, the method further comprises using a three dimensional template to identify at least one therapeutic agent.

In a further embodiment, the invention provides for a method of determining a disease state in a subject comprising obtaining a biological sample and a sample suspected of containing diseased cells from the subject; contacting each sample with a probe that binds to a sequence in a gene associated with kinase phosphorylation; and comparing the binding of the probe in the biological sample with the binding of the probe in the diseased cell sample wherein binding of the probe with the biological sample but not the diseased cell sample is indicative of a disease state or risk for developing a disease state in a subject. In one aspect, the disease state may be cancer, autoimmunity, infectious disease, and genetic disease. In an aspect, the method further comprises identifying a disease therapy, monitoring treatment of a disease state, determining a therapeutic response, identifying molecular targets for pharmacological intervention, and making determinations such as prognosis, disease progression, response to particular drugs and to stratify patient risk. In an additional aspect, the method further comprises determining a proliferation index, metastatic spread, genotype, phenotype, disease diagnosis, drug susceptibility, drug resistance, subject status and treatment regimen. In another aspect, the biological sample is blood, saliva, urine, bone marrow, serum, lymph, cerebrospinal fluid, sputum, stool, organ tissue, ejaculate sample, an organ sample, a tissue sample, an alimentary/gastrointestinal tract tissue sample, a liver sample, a skin sample, a lymph node sample, a kidney sample, a lung sample, a muscle sample, a bone sample, or a brain sample, a stomach sample, a small intestine sample, a colon sample, a rectal sample, or a combination thereof. In a further, aspect, the cancer is selected from an alimentary/gastrointestinal tract cancer, a liver cancer, a skin cancer, a breast cancer, an ovarian cancer, a prostate cancer, a lymphoma, a leukemia, a kidney cancer, a lung cancer, an esophageal cancer, a muscle cancer, a bone cancer, or a brain cancer. In certain aspects, the cancer is breast cancer and the breast cancer is ER+ breast cancer. In an aspect, the drug is a chemotherapeutic drug, an antibiotic, or an anti-inflammatory drug. In another aspect, the subject is a mammal and specifically, the human subject is a human.

In an additional embodiment, the present invention provides for a system for automated determination of an effective protein kinase inhibitor drug for a patient in need thereof comprising an input operable to receive patient sequence data for a protein kinase suspected of being associated with a disease state; a processor configured to apply the received sequence data to a first database comprising three-dimensional models of crystal structures of protein kinases, the processor configured to provide a display aligning a native protein kinase with the patient's protein kinase sequence, thereby identifying a region in the three-dimensional crystal structure of the kinase where the patient's kinase differs from the native kinase. In one aspect, the method further comprises a processor for input from a second database, wherein the second database comprises a plurality of protein kinase inhibitor drugs, thereby allowing stratification of one or more drug treatment options in a report based on the output status of the patient sequence data and the protein kinase inhibitor drugs. In an additional aspect, the patient is a cancer patient. In another aspect, the kinase is a tyrosine kinase.

In one embodiment, the present invention provides for a method of determining a therapeutic regimen for a patient comprising utilizing the system described above to determine one or more drugs for which the patient will be responsive and administering the one or more drugs to the patient based on the stratifying. In another aspect, the stratifying further comprises ranking one or more drug treatment options with a higher likelihood of efficacy or with a lower likelihood of efficacy. In another aspect, the stratifying further comprises ranking one or more drug treatment options with a higher likelihood of developing drug resistance of a lower likelihood of developing drug resistance. In a further aspect, the stratifying is indicated by color coding the listed drug treatment options on the report based on a rank of a predicted efficacy or resistance of the drug treatment options. In one aspect, the annotating comprises using information from a commercial database. In a further aspect, the annotating comprises providing a link to information on a clinical trial for a drug treatment option in the report. In one aspect, the annotating comprises adding information to the report selected from the group consisting of one or more drug treatment options, scientific information regarding one or more drug treatment options, one or more links to scientific information regarding one or more drug treatment options, one or more links to citations for scientific information regarding one or more drug treatment options, and clinical trial information regarding one or more drug treatment options.

In an additional embodiment, the present invention provides for a system for automated determination of an effective protein kinase inhibitor drug for a patient in need thereof comprising a database; and a processor circuit in communication with the database, the processor circuit configured to receive patient sequence data for a protein kinase suspected of being associated with a disease state; identify data indicative of a disease state within the database; store the data indicative of the disease state in the database; organize the data indicative of the disease state based on disease state; analyze the data indicative of the disease state to generate a treatment option based on the disease state and protein kinase inhibitor drug; and cause the treatment option and the organized data to be displayed.

In a further embodiment, the present invention provides for a method of determining a second course of therapy for a subject having developed resistance for a first course of therapy comprising identifying a mutation for resistance to the first course of therapy by genomic and/or three-dimensional crystallographic analysis; and determining a drug for the second course of therapy based on a search of a database of existing drugs, thereby identifying the second course of therapy.

In one embodiment, the present invention provides for a method of determining a second course of therapy for a subject having developed resistance for a first course of therapy comprising identifying a mutation for resistance to the first course of therapy by genomic and/or three-dimensional crystallographic analysis; and determining a drug for the second course of therapy based on a search of a crystal structure library database to identify a scaffold for a drug candidate as the second course of therapy, thereby identifying the second course of therapy. In an aspect, the determining step is uses a quantum computer.

In an additional embodiment, the present invention provides for a method for identifying a drug candidate comprising: identifying a mutation for resistance to a first course of therapy by genomic and/or three-dimensional crystallographic analysis; and determining a drug for the second course of therapy based on a search of a database of existing drugs and the genomic and/or three-dimensional crystallographic analysis, thereby identifying a drug candidate.

BRIEF DESCRIPTION OF THE DRAWINGS

FIG. 1A. The unique 3D pattern for fast sorting of scaffolds. FIG. 1B. The unique 3D hydrogen bond pattern with the scaffolds, including imatinib. FIG. 1C. The unique 3D hydrogen bond pattern in the target for binding the scaffold. FIG. 1D. The unique 3D pattern (subgraphs) of the scaffold to identify target specific binding pockets. FIG. 1E. The unique 3D pattern of the target which allow the algorithm to fast walk through the polypeptide chain of the target.

FIG. 2A. The identification of the phosphorylation sites on the target, including the activation loop. FIG. 2B. The selection of a unique 3D pattern within the DFG motif of the target to identify intermediate DFG conformations. FIG. 2C. The unique 3D pattern of the hydrophobic core of the target to identify a common drug resistance mutations.

FIGS. 3A-3F show the prediction of a specificity profile of a small molecule kinase inhibitor. FIG. 3A. Identification of the three dimensional network of selected constant (conserved) amino acids in the target. FIG. 3B. Identification of the three dimensional network of the variable (non-conserved) residues of the target. FIG. 3C. Selection of unique 3D pattern combinations for the prediction of the specificity profile for dasatimib. FIG. 3D. The unique combination of 3D patterns defining specific chemical interactions of the target and inhibitor to predict low and high affinities of nilotinib. FIG. 3E. The 3D structure of masitinib fitted onto the crystal structure of imatinib. FIG. 3F. Experimental versus computation specificity profiles for masitinib.

FIG. 4A. Evidence of the D816 mutation in KIT. FIG. 4B. Building and regularizing the model of the mutant. FIG. 4C. Pattern matching of the model to determine DFG in, out and intermediate conformation.

DETAILED DESCRIPTION OF THE INVENTION

Figure 1A:
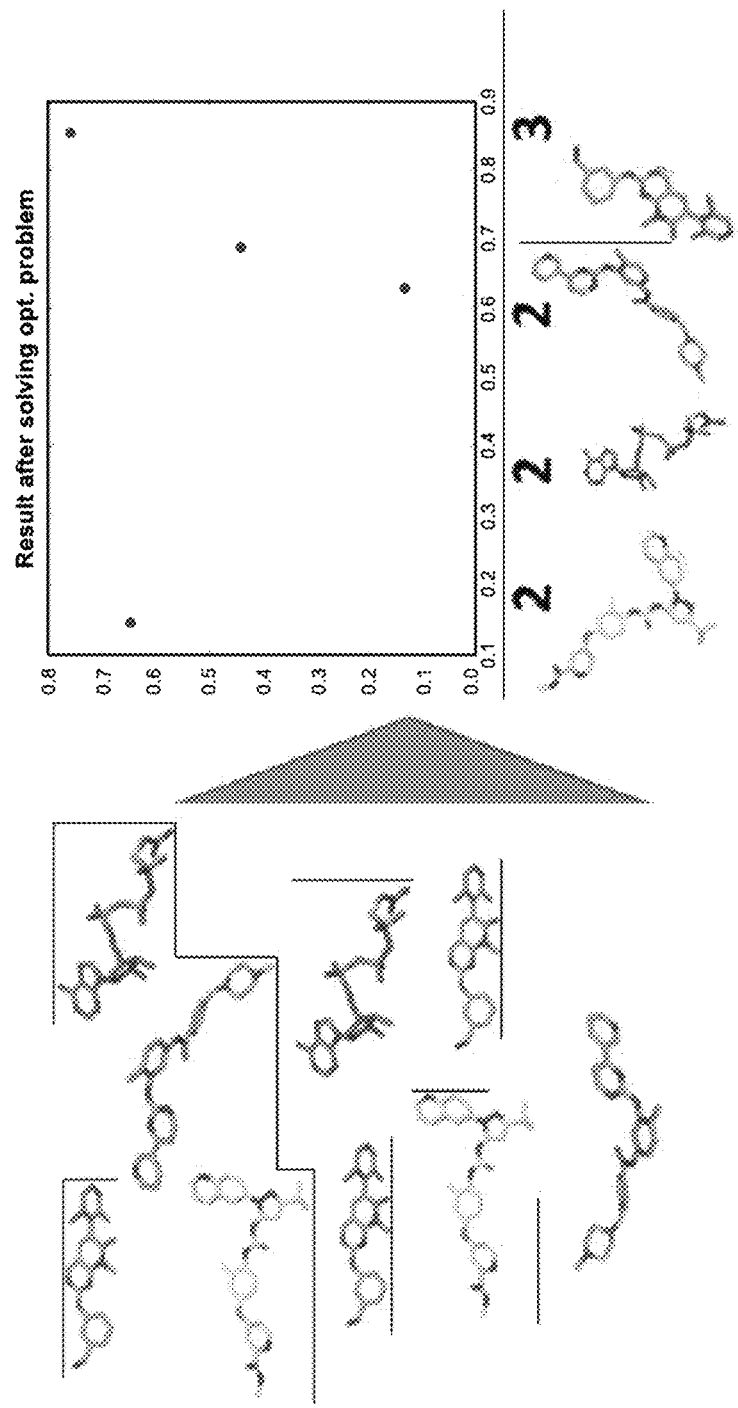
FIGS. 1A-1E show the use of the 3D pattern matching algorithm for the selection of therapeutic agents to target a specific kinase mutation.

The present invention relates to the seminal discovery of a method for identifying a treatment regimen for a patient diagnosed with cancer, predicting patient resistance to therapeutic agents and identifying new therapeutic agents. Specifically, the present invention relates to the use of an algorithm to identify a mutation in a kinase, determine if the mutation is an activation or resistance mutation and then to suggest an appropriate therapeutic regimen. The invention also relates to the use of a pattern matching algorithm and a crystal structure library to predict the functionality of a gene mutation, predict the specificity of small molecule kinase inhibitors and for the identification of new therapeutic agents.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. The definitions set forth below are for understanding of the disclosure but shall in no way be considered to supplant the understanding of the terms held by those of ordinary skill in the art.

A kinase is a type of enzyme that catalyzes the transfer of phosphate groups from high-energy, phosphate-donating molecules to specific substrates. Kinases are critical in metabolism, cell signaling, protein regulation, cellular transport, secretory processes, and countless other cellular pathways. Kinases mediate the transfer of a phosphate moiety from a high energy molecule (such as ATP) to their substrate molecule. Kinases are needed to stabilize this reaction because the phosphoanhydride bond contains a high level of energy. Kinases properly orient their substrate and the phosphoryl group within in their active sites, which increases the rate of the reaction. Additionally, they commonly use positively charged amino acid residues, which electrostatically stabilize the transition state by interacting with the negatively charged phosphate groups. Alternatively, some kinases utilize bound metal cofactors in their active sites to coordinate the phosphate groups.

Eukaryotic protein kinases are enzymes that belong to a very extensive family of proteins which share a conserved catalytic core common with both serine/threonine and tyrosine protein kinases. There are a number of conserved regions in the catalytic domain of protein kinases. In the N-terminal extremity of the catalytic domain there is a glycine-rich stretch of residues in the vicinity of a lysine residue, which has been shown to be involved in ATP binding. In the central part of the catalytic domain there is a conserved aspartic acid residue which is important for the catalytic activity of the enzyme.

The crystal structure 1ATP contains the mouse PKA catalytic (C) subunit, inhibitor protein PKI, the ATP analog ANP (CPK wireframe), and two manganese ions. In addition to the protein kinase catalytic domain (residues 43-297), the C subunit contains amino-terminal (residues 1-43) and carboxy-terminal (residues 298-350) sequences. The protein kinase fold of catalytic domains of eukaryotic protein kinases comprises a small lobe and a large lobe with a catalytic cleft, marked by the bound ANP molecule, is located between them. The small lobe binds ATP and the large lobe binds the protein substrate, modeled here by the inhibitor peptide PKI. PKI has an alanine substituted for the serine in the phosphorylation motif RRxS, and thus is unable to be phosphorylated.

The catalytic domain (i.e., protein kinase domain) is comprised of twelve subdomains:

Subdomain I contains two beta strands connected by the glycine-rich ATP-binding loop with the motif GxGxxG shown.

Subdomain II contains an invariant lysine that interacts with the phosphates of ATP.

Subdomain III is an alpha helix (helix C in bovine PKA) that connects to many parts of the kinase, and its orientation is critical for activity. In the active conformation of the kinase the nearly invariant glutamate in Subdomain III forms a salt bridge with the invariant lysine of Subdomain II. This salt bridge couples subdomain III to ATP.

Subdomain IV contains a beta strand and contributes to the core structure of the small lobe.

Subdomain V contains a hydrophobic beta strand in the small lobe and an alpha helix in the large lobe. The sequence that links these two secondary structures not only links together the small and large lobes of the kinase, but also contributes residues to the ATP binding pocket and also for peptide substrate binding. In PKA Glu 127 interacts with both the ribose of ATP and the first Arg in the phosphorylation motif RRxS of a peptide substrate.

Subdomain VIa is a long alpha helix in the large lobe that parallels the alpha helix of subdomain IX.

Subdomain VIb contains the catalytic loop with the conserved motif HRDLKxxN (In PKA the H is a Y, instead). The D of this motif is the catalytic base that accepts the hydrogen removed from the hydroxyl group being phosphorylated. Note the proximity of the glutamate residue to peptide residue that will be phosphorylated, here represented by an alanine in the inhibitor peptide. A substrate peptide would contain a serine instead of the alanine, and the hydroxyl group would narrow the gap between the substrate and the glutamate.

Subdomain VII contains two beta strands link by the Mg-binding loop with the DFG motif. The Aspartate in this motif chelates a $Mg^{2+}$ ion ($Mn^{2+}$ in the 1ATP crystal structure) that bridges the gamma and beta phosphates of ATP and positions the gamma phosphate for transfer to the substrate.

Subdomain VIII contains several important features. The APE motif is located at the carboxyl end of this subdomain and the glutamate in this motif forms a salt bridge with an arginine in in Subdomain XI. This salt bridge is critical for forming the stable kinase core and it provides an anchor for the movement of the activation loop. In many protein kinases there is a phosphorylatable residue seven to ten residues upstream of the APE motif. In PKA it is a phosphothreonine, which forms an ionic bond with the arginine in the YRDLKPEN motif of the catalytic loop and helps to position it for catalysis. Kinases that don't have a phosphorylatable residue in this loop often have an acidic residue that can form the salt bridge. Between the phosphorylated residue and the APE motif lies the P+1 loop, which interacts with the residue adjacent to the phosphorylated residue of the peptide substrate. The "P" residue is the one that is phosphorylated in the substrate, and the "P+1" residue is the next residue in the sequence.

Subdomain IX is a very hydrophobic alpha helix (helix F in mammalian PKA). It contains an invariant aspartate residue that is discussed below.

Subdomain X and Subdomain XI contain three alpha helices (G, H, and I in mammalian PKA) that form the kinase core and which are involved in binding substrate proteins.

Functional structures that involve residues from more than one subdomain have been recognized by biochemical and molecular genetic studies coupled with three-dimensional structures of protein kinases.

The activation loop comprises amino acid residues between the DFG motif in subdomain VII to the APE motif in subdomain VIII. As its name implies, it is involved in switching the activity of the kinase on and off. When the phosphorylatable residue in subdomain VIII is phosphorylated, the activation loop is positioned such that the active site cleft is accessible, the magnesium loop (DFG motif) and catalytic loop (HRDLKPxxN motif) are properly positioned for catalysis, and the P+1 loop can interact with the peptide substrate. The activation loop takes on a variety of conformations in inactive kinases that disrupt one or all of these conformations.

Two hydrophobic "spines" are important for the structure of active conformation of protein kinases. They are composed of amino acid residues that are non-contiguous in the primary structure. The catalytic spine includes the adenine ring of ATP. In PKA it comprises residues A70, V57, ATP, L173, 1174, L172, M128, M231, and L227, and it is directly anchored to amino end of helix F (Subdomain IX) The regulatory spine contains residues L106, L95, F185, Y164, and it is anchored to helix F via a hydrogen bond between the invariant aspartate in helix F and the backbone nitrogen of Y164. This spine is assembled in the active conformation and disorganized in inactive conformations.

The "gatekeeper" residue is a part of subdomain V (blue) and it is located deep in the ATP-binding pocket (Subdomain I with its ATP binding loop are shown in yellow). The size of the gatekeeper residue determines the size of the binding pocket, and it is thus a gatekeeper for which nucleotides, ATP analogs, and inhibitors can bind. In PKA and about 75% of all kinases it is a large residue, such as leucine, phenylalanine or methionine as seen here. In the remaining kinases, especially tyrosine kinases, the residue is larger, such as threonine or valine. The gatekeeper's location is between the two hydrophobic spines (gatekeeper is chartreuse, catalytic spine is blue, regulatory spine is orchid). Mutation of this residue in some kinases leads to activation of the kinase via enhanced autophosphorylation of the activation loop, and the unregulated kinase activity promotes cancer. The gatekeeper's interaction with the two spines affects the orientation of the catalytic, magnesium binding, and activation loops.

While active conformations of protein kinases are very similar, there is great variation in the inactive conformations of protein kinases, but all involve misalignment of one or more of the structures, subdomain III (C-helix in PKA) and the catalytic, magnesium binding, and activation loops.

The following is a list of human proteins containing the protein kinase domain:

AAK1; ABL1; ABL2; ACVR1; ACVR1B; ACVR1C; ACVR2A; ACVR2B; ACVRL1; ADCK1; ADCK2; ADCK3; ADCK4; ADCK5; ADRBK1; ADRBK2; AKT1; AKT2; AKT3; ALPK1; ALPK2; ALPK3; STRADB; CDK15; AMHR2; ANKK1; ARAF; ATM; ATR; AURKA; AURKB; AURKC; AXL; BCKDK; BLK; BMP2K; BMPR1A; BMPR1B; BMPR2; BMX; BRAF; BRSK1; BRSK2; BTK; BUB1; C21orf7; CALM1; CALM2; CALM3; CAMK1; CAMK1D; CAMK1G; CAMK2A; CAMK2B; CAMK2D; CAMK2G; CAMK4; CAMKK1; CAMKK2; CAMKV; CASK; CDK20; CDK1; CDK11B; CDK11A; CDK13; CDK19; CDC42BPA; CDC42BPB; CDC42BPG; CDC7; CDK10; CDK2; CDK3; CDK4; CDK5; CDK6; CDK7; CDK8; CDK9; CDK12; CDK14; CDK16; CDK17; CDK18; CDKL1; CDKL2; CDKL3; CDKL4; CDKL5; CHEK1; CHEK2; CHUK; CIT; CKB; CKM; CLK1; CLK2; CLK3; CLK4; CSF1R; CSK; CSNK1A1; CSNK1A1L; CSNK1D; CSNK1E; CSNK1G1; CSNK1G2; CSNK1G3; CSNK2A1; CSNK2A2; DAPK1; DAPK2; DAPK3; DCLK1; DCLK2; DCLK3; DDR1; DDR2; DMPK; DYRK1A; DYRK1B; DYRK2; DYRK3; DYRK4; EGFR; EIF2AK1; EIF2AK2; EIF2AK3; EIF2AK4; ELK1; EPHA1; EPHA2; EPHA3; EPHA4; EPHA5; EPHA6; EPHA7; EPHA8; EPHB1; EPHB2; EPHB3; EPHB4; ERBB2; ERBB3; ERBB4; ERN1; ERN2; FER; FES; FGFR1; FGFR2; FGFR3; FGFR4; FGR; FLT1; FLT3; FLT4; FYN; GAK; GRK1; GRK4; GRK5; GRK6; GRK7; GSK3A; GSK3B; GUCY2C; GUCY2D; GUCY2E; GUCY2F; HCK; HIPK1; HIPK2; HIPK3; HIPK4; HUNK; ICK; IGF1R; IGF2R; IKBKB; IKBKE; ILK; INSR; IRAK1; IRAK2; IRAK3; IRAK4; ITK; JAK1; JAK2; JAK3; KALRN; KDR; SIK3; KSR2; LATS1; LATS2; LIMK1; LCK; LIMK2; LRRK1; LRRK2; LYN; MAK; MAP2K1; MAP2K2; MAP2K3; MAP2K4; MAP2K5; MAP2K6; MAP2K7; MAP3K1; MAP3K10; MAP3K11; MAP3K12; MAP3K13; MAP3K14; MAP3K15; MAP3K2; MAP3K3; MAP3K4; MAP3K5; MAP3K6; MAP3K7; MAP3K8; MAP3K9; MAP4K1; MAP4K2; MAP4K3; MAP4K4; MAP4K5; MAPK1; MAPK10; MAPK12; MAPK13; MAPK14; MAPK15; MAPK3; MAPK4; MAPK6; MAPK7; MAPK8; MAPK9; MAPKAPK2; MAPKAPK3; MAPKAPK5; MARK1; MARK2; MARK3; MARK4; MAST1; MAST2; MAST3; MAST4; MASTL; MELK; MERTK; MET; MINK1; MKNK1; MKNK2; MLKL; MOS; MST1R; MST4; MTOR; MYLK; MYLK2; MYLK3; MYLK4; NEK1; NEK10; NEK11; NEK2; NEK3; NEK4; NEK5; LOC100506859; NEK6; NEK7; NEK8; NEK9; MGC42105; NLK; NRK; NRK1; NTRK2; NTRK3; NUAK1; NUAK2; OBSCN; OXSR1; PAK1; PAK2; PAK3; PAK4; PAK6; PAK7; PASK; PBK; PDGFRA; PDGFRB; PDIK1L; PDPK1; PHKA1; PHKB; PHKG1; PHKG2; PIK3R4; PIM1; PIM2; PIM3; PINK1; PKMYT1; PKN1; PKN2; PKN3; PLK1; PLK2; PLK3; PLK4; PNCK; PRKAA1; PRKAA2; PRKACA; PRKACB; PRKACG; PRKCA; PRKCB; PRKCD; PRKCE; PRKCG; PRKCH; PRKCI; PRKCQ; PRKCZ; PRKD1; PRKD2; PRKD3; PRKG1; PRKG2; PRKX; LOC389906; PRKY; PRPF4B; PSKH1; PSKH2; PTK2; PTK2B; RAF1; RAGE; RET; RIP3; RIPK1; RIPK2; RIPK3; RIPK4; ROCK1; ROCK2; ROR1; ROR2; ROS1; RPS6KA1; RPS6KA2; RPS6KA3; RPS6KA4; RPS6KA5; RPS6KA6; RPS6KB1; RPS6KB2; RPS6KC1; RPS6KL1; RYK; SCYL1; SCYL2; SCYL3; SGK1; LOC100130827; SGK196; SGK2; SGK3; SGK494; SIK1; SIK2; SLK; SNRK; SPEG; SRC; SRPK1; SRPK2; SRPK3; STK10; STK11; STK16; STK17A; STK17B; STK19; STK24; STK25; STK3; STK31; STK32A; STK32B; STK32C; STK33; STK35; STK36; STK38; STK38L; STK39; STK4; STK40; SYK; TAOK1; TAOK2; TAOK3; TBCK; TBK1; TEC; TESK1; TESK2; TGFBR1; TGFBR2; TIE1; TIE2; TLK1; TLK2; TNIK; TNK1; TNK2; TSSK1B; TSSK2; TSSK3; TSSK4; TTBK1; TTBK2; TTK;

TWF2; TXK; TYK2; TYRO3; UHMK1; ULK1; ULK2; ULK3; ULK4; VRK1; VRK2; VRK3; WEE1; WEE2; WNK1; WNK2; WNK3; WNK4; YES1; ZAK; ZAP70.

Kinases are used extensively to transmit signals and regulate complex processes in cells. Phosphorylation of molecules can enhance or inhibit their activity and modulate their ability to interact with other molecules. The addition and removal of phosphoryl groups provides the cell with a means of control because various kinases can respond to different conditions or signals. Mutations in kinases that lead to a loss-of-function or gain-of-function can cause cancer and disease in humans, including certain types of leukemia and neuroblastomas, glioblastoma, spinocerebellar ataxia (type 14), forms of agammaglobulinaemia, and many others.

A growing interest in developing orally active protein-kinase inhibitors has recently culminated in the approval of the first of these drugs for clinical use. Protein kinases have now become the second most important group of drug targets, after G-protein-coupled receptors. Identification of the key roles of protein kinases in signaling pathways leading to development of cancer has caused pharmacological interest to concentrate extensively on targeted therapies as a more specific and effective way for blockade of cancer progression. Over the past 15 years protein kinases have become the pharmaceutical industry's most important class of drug target in the field of cancer. Some 20 drugs that target kinases have been approved for clinical use over the past decade, and hundreds more are undergoing clinical trials.

Examples of kinase inhibitors include: Afatinib, Axitinib, Bevacizumab, Bosutinib, Cetuximab, Crizotinib, Dasatinib, Erlotinib, Fostamatinib, Gefitinib, Ibrutinib, Imatinib, Lapatinib, Lenvatinib, Masitinib, Mubritinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib and Vemurafenib.

In one embodiment, the present invention provides a method for identifying a therapeutic regimen or predicting resistance to a therapeutic regimen for a patient with cancer comprising obtaining a biologic sample from the patient; identifying at least one mutation in the gene sequence from the sample; using a pattern matching algorithm to determine if the at least one mutation is an activation mutation or a resistance mutation; and using the pattern matching algorithm and a crystal structure library to identify therapeutic agents to target the activating mutation or for which the patient is resistant; thereby identifying a therapeutic regimen or predicting resistance to a therapeutic regimen. In one aspect, the biological sample is blood, saliva, urine, bone marrow, serum, lymph, cerebrospinal fluid, sputum, stool, organ tissue or ejaculate sample. In one aspect, the at least one mutation is identified by sequence analysis. In another aspect, the at least one mutation is in the gene sequence of a receptor or a kinase. In another aspect, the at least one mutation is in the catalytic domain of a kinase. In an additional aspect, the at least one mutation results in a novel kinase conformation. In a specific aspect, the at least one mutation is in the DFG domain. In an aspect the receptor is an estrogen receptor. In certain aspects, the estrogen receptor is ESR1 or ESR2. In a further aspect, the crystal structure library comprises a protein crystal structure database and a therapeutic agent crystal structure database. In an additional aspect, the algorithm is subjected to machine learning. In one aspect, the at least one mutation comprises an activation mutation or a resistance mutation. In another aspect, the at least one mutation comprises a mutation in a kinase or a receptor. In certain aspects, the receptor is an estrogen receptor 1 (ESR1) or an estrogen receptor 2 (ESR2). In another aspect, the therapeutic regimen comprises a kinase inhibitor and/or a chemotherapeutic agent.

As used herein, the term "biological specimen" refers to any human specimen type. Examples of biological specimen include DNA, RNA, cells, tissues, organs, gametes, bodily products (teeth, hair, nail clippings, sweat, urine feces), blood and blood fractions (plasma serum red blood cells), saliva, bone marrow, lymph, cerebrospinal fluid, sputum, or ejaculate sample.

Techniques are well known in the art to detect DNA, RNA and protein mutations. Such techniques include DNA, RNA and protein sequencing.

Mutations are changes in DNA or protein sequence as compared to wild type. Mutations include insertions, deletions and point mutations. Many mutations have been identified in tumors. Identifying "actionable mutations" requires a lengthy statistical data analysis of one dimensional genomic data gathered from many cancer patients. However, these actionable mutations are quickly outdated due to the rapid progression of the cancer. Examples of mutations identified in cancer include activating mutations and resistance mutations. Activating mutations are responsible for the onset or progression of a tumor. Resistance mutations confer resistance to the tumor to therapeutic agents rendering the therapeutic agents ineffective in treating the tumor. The mechanism of drug resistance is highly diverse and differs between patients making it difficult to determine which therapeutic agents to use in further therapy once resistance is acquired.

As used herein, the term "therapeutic regimen" refers to any course of therapy using at least one therapeutic agent in the treatment of a disease or disorder.

As used herein, the term "therapeutic agent" any molecule or compound used in the treatment of a disease or disorder. The therapeutic agent maybe a kinase inhibitor. Examples of kinase inhibitor include Afatinib, Axitinib, Bevacizumab, Bosutinib, Cetuximab, Crizotinib, Dasatinib, Erlotinib, Fostamatinib, Gefitinib, Ibrutinib, Imatinib, Lapatinib, Lenvatinib, Masitinib, Mubritinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib and Vemurafenib.

Where the disease or disorder is cancer, the therapeutic agent is a chemotherapeutic drug. Examples of chemotherapeutic drugs include aromatase inhibitors, tamoxifene, Raloxifene, a competitor of estrogen in its ER binding site, antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine, antibodies such as trastuzumab; bevacizumab, OSI-774, Vitaxin; alkaloids, including, microtubule inhibitors (e.g., Vincristine, Vinblastine, and Vindesine, etc.), microtubule stabilizers (e.g., Paclitaxel (Taxol), and Docetaxel, Taxotere, etc.), and chromatin function inhibitors, including, topoisomerase inhibitors, such as, epipodophyllotoxins (e.g., Etoposide (VP-16), and Teniposide (VM-26), etc.), agents that target topoisomerase I (e.g., Camptothecin and Isirinotecan (CPT-11), etc.); covalent DNA-binding agents (alkylating agents), including, nitrogen mustards (e.g., Mechlorethamine, Chlorambucil, Cyclophosphamide, Ifosphamide, and Busulfan (Myleran), etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); noncovalent DNA-binding agents (antitumor antibiotics), including, nucleic acid inhibitors (e.g., Dactinomycin (Actinomycin D)), anthracyclines (e.g., Daunorubicin (Daunomycin, and Cerubidine), Doxorubicin (Adriamycin), and Idarubicin (Idamycin)), anthracenediones (e.g., anthracycline analogues, such as, (Mitoxantrone)), bleomycins (Blenoxane), etc., and plicamycin (Mithramycin); antimetabolites, including, antifolates (e.g., Methotrexate, Folex, and Mexate), purine antimetabolites (e.g., 6-Mercaptopurine (6-MP, Purinethol), 6-Thioguanine (6-TG), Azathioprine, Acyclovir, Ganciclovir, Chlorodeoxyadenosine, 2-Chlorodeoxyadenosine (CdA), and 2'-Deoxycoformycin (Pentostatin), etc.), pyrimidine antagonists (e.g., fluoropyrimidines) (e.g., 5-fluorouracil (Adrucil), 5-fluorodeoxyuridine (FdUrd) (Floxuridine)) etc.), and cytosine arabinosides (e.g., Cytosar (ara-C) and Fludarabine); enzymes, including, L-asparaginase; hormones, including, glucocorticoids, such as, antiestrogens (e.g., Tamoxifen, etc.), non-steroidal antiandrogens (e.g., Flutamide); platinum compounds (e.g., Cisplatin and Carboplatin); monoclonal antibodies conjugated with anticancer drugs, toxins, and/or radionuclides, etc.; biological response modifiers (e.g., interferons (e.g., IFN-alpha.) and interleukins (e.g., IL-2).

Cancer is a group of diseases involving abnormal cell growth with the potential to invade or spread to other parts of the body. Cancer is characterized by several biochemical mechanisms including self-sufficiency in growth signaling, insensitivity to anti-growth signals, evasion of apoptosis, enabling of a limitless replicative potential, induction and sustainment of angiogenesis and activation of metastasis and invasion of tissue.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult;

Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

A 3D pattern matching algorithm functions to analyze the 3D architecture of proteins and drug targets. Specifically, the algorithm identifies differences due to mutations or post translational modifications of a protein as well as different conformational states and unique intermediate states created by cancer activating mutations and or drug resistance mutations in a biological sample when compared to a proprietary database.

The use of a proprietary crystal structure library and unique training lessons teach (i.e., machine learning) the pattern matching algorithm to predict the functionality of any kinase mutation, predict specificity of a small molecule kinase inhibitor and drug development by the prediction of virtual molecules to inhibit kinases identified by previously unknown intermediate states of kinase catalytic cores resulting from activating cancer mutations. Further, the predictive algorithm methodology enables the rapid design of new drug candidates based on the specificity profile for the predicted functionality of a mutation.

The protein crystal structure library includes the crystal structures of proteins, including kinases and receptors as well as drug ligands.

The algorithm comprises pattern matching and machine learning features to enable the accurate prediction of the functionality of the identified mutation. The analysis also enables the prediction of which therapeutic agents would target the identified mutations.

In one embodiment, the present invention relates to a method of determining risk for developing resistance or the development of resistance to a therapeutic regimen in an ER+ breast cancer patient comprising obtaining a biological sample and a tumor sample from the patient; contacting each sample with a probe that binds to a sequence in a gene associated with kinase phosphorylation; and comparing the binding of the probe in the biological sample with the binding of the probe in the tumor sample wherein binding of the probe with the biological sample but not the tumor sample is indicative of a tumor that is at risk for developing resistance to a therapeutic regimen. In one aspect, the sample is obtained from the patient following a course of therapy and wherein the course of therapy is ongoing for at least about 1 month to 6 months at the time the sample is obtained. In another aspect, the sample is obtained at intervals throughout the course of therapy. In one aspect, the subject is a human. In a further aspect, the biological sample is blood, saliva, urine, bone marrow, serum, lymph, cerebrospinal fluid, sputum, stool, organ tissue or ejaculate sample. In an additional aspect, the probe detects a mutation in the gene sequence. In a specific aspect, the mutation is a point mutation. In another aspect, the biological sample is a tumor sample and specifically, the tumor sample is a liquid biopsy or a sample of circulating tumor cells (CTCs).

In another aspect, the probe detects a deletion in the gene sequence. In one aspect, the deletion is about 2 to 12 amino acids. In a further aspect, the probe detects a deletion and a single point mutation in the gene sequence. In one aspect probe is at least about 1000 nucleotides, from about 300 to 500 nucleotides or at least about 150 nucleotides for more than one region of the gene sequence. In further aspect, the gene sequence is an ESR receptor gene sequence. In a specific aspect, the ESR receptor is ESR1 or ESR2. In certain aspects, the ESR1 receptor has a point mutation at Y537, E380, L536, and/or D538. In specific aspects the ESR1 mutation is Y537S, Y537A, Y537E or Y537K. In another aspect, the ESR2 receptor has a point mutation at V497 and specifically, the mutation is V497M.

In a further aspect, the therapeutic regimen is treatment with an aromatase inhibitor. In a specific aspect, the therapeutic regimen is treatment with a tamoxifene, Raloxifene and/or a competitor of estrogen in its ER binding site.

In another aspect, the method further comprises predicting a second form of therapy. In certain aspects, the second form of therapy is provided to the patient prior to completion of a therapeutic regimen with a first form of therapy. In another aspect, the first form of therapy is an aromatase inhibitor and the second form of therapy is a non-aromatase inhibitor chemotherapeutic drug. In an additional aspect, the non-aromatase inhibitor chemotherapeutic drug may be antimetabolites, such as methotrexate, DNA cross-linking agents, such as cisplatin/carboplatin; alkylating agents, such as canbusil; topoisomerase I inhibitors such as dactinomycin; microtubule inhibitors such as taxol (paclitaxol), a vinca alkaloid, mitomycin-type antibiotic, bleomycin-type antibiotic, antifolate, colchicine, demecolcine, etoposide, taxane, anthracycline antibiotic, doxorubicin, daunorubicin, caminomycin, epirubicin, idarubicin, mitoxanthrone, 4-dimethoxy-daunomycin, 11-deoxydaunorubicin, 13-deoxydaunorubicin, adriamycin-14-benzoate, adriamycin-14-octanoate, adriamycin-14-naphthaleneacetate, amsacrine, carmustine, cyclophosphamide, cytarabine, etoposide, lovastatin, melphalan, topetecan, oxalaplatin, chlorambucil, methotrexate, lomustine, thioguanine, asparaginase, vinblastine, vindesine, tamoxifen, or mechlorethamine, antibodies such as trastuzumab; bevacizumab, OSI-774, Vitaxin; alkaloids, including, microtubule inhibitors (e.g., Vincristine, Vinblastine, and Vindesine, etc.), microtubule stabilizers (e.g., Paclitaxel (Taxol), and Docetaxel, Taxotere, etc.), and chromatin function inhibitors, including, topoisomerase inhibitors, such as, epipodophyllotoxins (e.g., Etoposide (VP-16), and Teniposide (VM-26), etc.), agents that target topoisomerase I (e.g., Camptothecin and Isirinotecan (CPT-11), etc.); covalent DNA-binding agents (alkylating agents), including, nitrogen mustards (e.g., Mechlorethamine, Chlorambucil, Cyclophosphamide, Ifosphamide, and Busulfan (Myleran), etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); noncovalent DNA-binding agents (antitumor antibiotics), including, nucleic acid inhibitors (e.g., Dactinomycin (Actinomycin D)), anthracyclines (e.g., Daunorubicin (Daunomycin, and Cerubidine), Doxorubicin (Adriamycin), and Idarubicin (Idamycin)), anthracenediones (e.g., anthracycline analogues, such as, (Mitoxantrone)), bleomycins (Blenoxane), etc., and plicamycin (Mithramycin); antimetabolites, including, antifolates (e.g., Methotrexate, Folex, and Mexate), purine antimetabolites (e.g., 6-Mercaptopurine (6-MP, Purinethol), 6-Thioguanine (6-TG), Azathioprine, Acyclovir, Ganciclovir, Chlorodeoxyadenosine, 2-Chlorodeoxyadenosine (CdA), and 2'-Deoxycoformycin (Pentostatin), etc.), pyrimidine antagonists (e.g., fluoropyrimidines (e.g., 5-fluorouracil (Adrucil), 5-fluorodeoxyuridine (FdUrd) (Floxuridine)) etc.), and cytosine arabinosides (e.g., Cytosar (ara-C) and Fludarabine); enzymes, including, L-asparaginase; hormones, including, glucocorticoids, such as, antiestrogens (e.g., Tamoxifen, etc.), non-steroidal antiandrogens (e.g., Flutamide); platinum compounds (e.g., Cisplatin and Carboplatin); monoclonal antibodies conjugated with anticancer drugs, toxins, and/or radionuclides, etc.; biological response modifiers (e.g., interferons (e.g., IFN-alpha.) and interleukins (e.g., IL-2).

In one aspect, the determination is performed on a computer. In another aspect, the gene sequence is in a database. In a certain aspect, the database contains sequences for the catalytic cores of protein kinases.

In a further embodiment, the present invention provides a method for identifying a drug candidate comprising identifying a mutation for resistance to a first drug by genomic and/or three-dimensional crystallographic analysis; and determining a second drug based on the mutation for resistance due to the first drug, by searching a crystal structure library database to identify a scaffold for a drug candidate as the second drug, thereby identifying a drug candidate. In one aspect, a pattern matching algorithm is used to search the crystal structure library.

In another embodiment, the present invention provides a method for predicting the specificity profile of a therapeutic agent comprising obtaining the crystal structure of the therapeutic agent; and using a pattern matching algorithm to identify targets of the therapeutic agent using a crystal structure library, thereby, predicting the specificity profile of a therapeutic agent. In one aspect, the crystal structure library comprises a protein crystal structure database. In another aspect, the protein crystal structure database comprises the crystal structure of kinases and receptors. In an aspect, the therapeutic agent is a kinase inhibitor. In one aspect, the kinase inhibitor is Afatinib, Axitinib, Bevacizumab, Bosutinib, Cetuximab, Crizotinib, Dasatinib, Erlotinib, Fostamatinib, Gefitinib, Ibrutinib, Imatinib, Lapatinib, Lenvatinib, Masitinib, Mubritinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib or Vemurafenib or a combination thereof. In another aspect, the therapeutic agent is a chemotherapeutic agent. In an additional aspect, the target is a kinase or a receptor. In one aspect, the target is a mutation in a gene sequence. In a further aspect, the gene mutation is in a kinase or a receptor. In certain aspects, the target is the catalytic domain of a kinase. In a specific aspect, the target is the DFG domain. In one aspect, the receptor is an estrogen receptor. In an additional aspect, the specificity profile is used in the selection of a treatment regimen for a patient in need thereof.

In a further embodiment, the present invention provides a method of treating a patient in need thereof comprising obtaining a biologic sample; identifying at least one mutation in a gene from the biologic sample; using a pattern matching algorithm and a crystal structure library to identify at least one therapeutic agent to target the at least one mutation; and administering the identified therapeutic agent to the patient, thereby treating the patient. In one aspect, the patient is diagnosed with cancer. In another aspect, at least 2 gene mutations are identified. In certain aspects, 2, 3, 4, 5, 6, 7, 8, 9, or 10 gene mutations are identified. In a further aspect, the gene mutations are identified by sequence analysis. In an aspect, the crystal structure library comprises the crystal structure of kinases, receptors and ligands. In one aspect, the target is a kinase or a receptor. In an additional aspect, more than one therapeutic agent is selected for the treatment regimen. In a further aspect the at least one chemotherapeutic agent. In certain aspects, one chemotherapeutic agent is a kinase inhibitor.

In a further embodiment, the invention provides for a method of determining a disease state in a subject comprising obtaining a biological sample and a sample suspected of containing diseased cells from the subject; contacting each sample with a probe that binds to a sequence in a gene associated with kinase phosphorylation; and comparing the binding of the probe in the biological sample with the binding of the probe in the diseased cell sample wherein binding of the probe with the biological sample but not the diseased cell sample is indicative of a disease state or risk for developing a disease state in a subject. In one aspect, the disease state may be cancer, autoimmunity, infectious disease, and genetic disease. In an aspect, the method further comprises identifying a disease therapy, monitoring treatment of a disease state, determining a therapeutic response, identifying molecular targets for pharmacological intervention, and making determinations such as prognosis, disease progression, response to particular drugs and to stratify patient risk. In an additional aspect, the method further comprises determining a proliferation index, metastatic spread, genotype, phenotype, disease diagnosis, drug susceptibility, drug resistance, subject status and treatment regimen. In another aspect, the biological sample is blood, saliva, urine, bone marrow, serum, lymph, cerebrospinal fluid, sputum, stool, organ tissue, ejaculate sample, an organ sample, a tissue sample, an alimentary/gastrointestinal tract tissue sample, a liver sample, a skin sample, a lymph node sample, a kidney sample, a lung sample, a muscle sample, a bone sample, or a brain sample, a stomach sample, a small intestine sample, a colon sample, a rectal sample, or a combination thereof. In a further, aspect, the cancer is selected from an alimentary/gastrointestinal tract cancer, a liver cancer, a skin cancer, a breast cancer, an ovarian cancer, a prostate cancer, a lymphoma, a leukemia, a kidney cancer, a lung cancer, an esophageal cancer, a muscle cancer, a bone cancer, or a brain cancer. In certain aspects, the cancer is breast cancer and the breast cancer is ER+ breast cancer. In an aspect, the drug is a chemotherapeutic drug, an antibiotic, or an anti-inflammatory drug. In another aspect, the subject is a mammal and specifically, the human subject is a human.

In an additional embodiment, the present invention provides for a system for automated determination of an effective protein kinase inhibitor drug for a patient in need thereof comprising an input operable to receive patient sequence data for a protein kinase suspected of being associated with a disease state; a processor configured to apply the received sequence data to a first database comprising three-dimensional models of crystal structures of protein kinases, the processor configured to provide a display aligning a native protein kinase with the patient's protein kinase sequence, thereby identifying a region in the three-dimensional crystal structure of the kinase where the patient's kinase differs from the native kinase. In one aspect, the method further comprises a processor for input from a second database, wherein the second database comprises a plurality of protein kinase inhibitor drugs, thereby allowing stratification of one or more drug treatment options in a report based on the output status of the patient sequence data and the protein kinase inhibitor drugs. In an additional aspect, the patient is a cancer patient. In another aspect, the kinase is a tyrosine kinase.

In one embodiment, the present invention provides for a method of determining a therapeutic regimen for a patient comprising utilizing the system described above to determine one or more drugs for which the patient will be responsive and administering the one or more drugs to the patient based on the stratifying. In another aspect, the stratifying further comprises ranking one or more drug treatment options with a higher likelihood of efficacy or with a lower likelihood of efficacy. In another aspect, the stratifying further comprises ranking one or more drug treatment options with a higher likelihood of developing drug resistance of a lower likelihood of developing drug resistance. In a further aspect, the stratifying is indicated by color coding the listed drug treatment options on the report based on a rank of a predicted efficacy or resistance of the drug treatment options. In one aspect, the annotating comprises using information from a commercial database. In a further aspect, the annotating comprises providing a link to information on a clinical trial for a drug treatment option in the report. In one aspect, the annotating comprises adding information to the report selected from the group consisting of one or more drug treatment options, scientific information regarding one or more drug treatment options, one or more links to scientific information regarding one or more drug treatment options, one or more links to citations for scientific information regarding one or more drug treatment options, and clinical trial information regarding one or more drug treatment options.

In an additional embodiment, the present invention provides for a system for automated determination of an effective protein kinase inhibitor drug for a patient in need thereof comprising a database; and a processor circuit in communication with the database, the processor circuit configured to receive patient sequence data for a protein kinase suspected of being associated with a disease state; identify data indicative of a disease state within the database; store the data indicative of the disease state in the database; organize the data indicative of the disease state based on disease state; analyze the data indicative of the disease state to generate a treatment option based on the disease state and protein kinase inhibitor drug; and cause the treatment option and the organized data to be displayed.

In a further embodiment, the present invention provides for a method of determining a second course of therapy for a subject having developed resistance for a first course of therapy comprising identifying a mutation for resistance to the first course of therapy by genomic and/or three-dimensional crystallographic analysis; and determining a drug for the second course of therapy based on a search of a database of existing drugs, thereby identifying the second course of therapy. In one aspect, the method further comprises preparing nucleic acid based probes that correlate with the mutation for the resistance to the first course of therapy.

In one embodiment, the present invention provides for a method of determining a second course of therapy for a subject having developed resistance for a first course of therapy comprising identifying a mutation for resistance to the first course of therapy by genomic and/or three-dimensional crystallographic analysis; and determining a drug for the second course of therapy based on a search of a crystal structure library database to identify a scaffold for a drug candidate as the second course of therapy, thereby identifying the second course of therapy. In an aspect, the determining step is uses a quantum computer.

In another embodiment, the present invention provides for a method for identifying a drug candidate comprising identifying a mutation for resistance to a first drug by genomic and/or three-dimensional crystallographic analysis; and determining a second drug based on the mutation for resistance due to the first drug, by searching a crystal structure library database to identify a scaffold for a drug candidate as the second drug, thereby identifying a drug candidate.

The invention in all its aspects is illustrated further in the following Examples. The Examples do not, however, limit the scope of the invention, which is defined by the appended claims.

EXAMPLES

Example I

Construction of a Human Protein Kinase

A library was constructed of all the human protein kinase structures that have been published in the Protein Data Bank. The database provided information regarding any mutations in the kinase, the location of any mutations within the three dimensional structure of the kinase as well as whether an approved drug has been crystalized with a kinase and an associated mutation. The library was assembled using a DNA SEQ script. The DNA SEQ script can be run (used) on the Protein Data Bank (PDB). All available PDB files that contain a human kinase structure are "pruned" (term "pruning" is referred to alteration of PDB file in very unique way) and aligned to the first crystal structure of protein kinase that is 1ATP. The script divides the protein from the ligand. The final library has the following structural files:

ZZxxxxx that represents all the protein kinases aligned (using DNA SEQ script).

AAxxxxx that represent all the ligands generated from co-crystallization to human kinase all aligned as the complex (ligand and kinase).

YYxxxxx is the alignment of all APO (no ligands) structures find among human kinase crystallized.

The key optimization problem set for the algorithm is to "reconstruct the complex from ZZxxxxx file and AAxxxxx file. During the process of reconstruction' the various criteria are being used which, in general, can be defined as "the teaching lessons". Correct reconstruction of the complex through a set of lessons provides the algorithm the path to learn (see [0100]).

This database provides guidance as to whether a mutation will interfere with the binding of a drug or clinical candidate for a kinase and predict a known drug or clinical candidate that should be used for that mutation. The database includes a functional alignment to a kinase structure that contains information regarding conformation close to the active state (i.e., active kinase conformation, ATP, ions, substrate and regulatory domain) to provide structure/function perspective. This database has been utilized to provide therapeutic recommendations, identify a potential risk factor, develop predictive guidance on previously known mutations and kinases for which the structure is unknown and drug development.

In one example, 2,139 crystal structures of human protein kinase catalytic domains were extracted from the database and aligned to the 1ATP crystal structure. Diverse kinase structures were overlayed and the resulting alignment at the ATP binding pocket was analyzed. Three key regions were analyzed: the hinge region, DFG specificity pocket and the ATP substrate.

Once a kinase mutation was identified by sequencing, the database was queried to determine if the structure of the kinase is known; if a structure with that mutation is known; if a structure of the kinase that contains bound ligands is known and if there is a clinical drug structure known, for either the wild type or mutated kinase. From this information guidance was derived for determining recommendations for mutation responsive/nonresponsive drug treatments.

In another example, the library was refined by analyzing the 2,139 aligned protein kinases for their rmsd versus the 1 ATP reference. RMSD is a specific parameter routinely used by crystallographers that represents: Root-Mean-Square Deviation of atomic positions. Deviation from two structures (specifically two atoms with each distinct XYZ positions) being compared—please refer to: en.wikipedia.org/wiki/Root-mean-square_deviation_of_atomic_positions.

In this example we compare the staurosporine, a nonspecific ligand for kinases (binds all), versus imatinib (Gleevec®) the specific ligand that binds to the specific conformation of the kinase targets (c-abl.c-kit and PDGF).

The 718,704 rmsd values were then averaged for each of the 336 residues in 1ATP. The average rmsd values were plotted against the sequence numbering. The kinase library was analyzed for overall similarity. Sequence rmsd cutoffs were used to truncate the alignment, the model altered the alignment of the ligand staurosporine. Structural impact of ligand binding, kinase library similarity-complexes, kinase library similarity—unliganded, staurosporine complexes only and imatinib (STI) complexes only were analyzed.

Example II

3D Pattern Matching Machine Learning Algorithm

The 3D pattern matching machine learning algorithm was developed using similar structures to define interactions, maximum common subgraph problem, reduction to a maximum clique problem, and branch and bound based algorithms.

The first objective was to compute MCS for every pair of molecules in the dataset; finds groups of "similar" molecules; represent the data set visually in a 3D space, so that "similar" molecules would be close to one another. MCS=Maximum Common Sub Graph. This definition is currently being used in pattern matching and machine learning. In a simple way it means that if man or women is perfectly dressed—the key elements combining and creating maximum Common Sub graph of Elegance/Style, must include: shoes, bag, dress, watch. Nobody cares about his/her underwear. Some designers/mathematician will eliminate the watch. Then if we run millions of them defining the maximum common sub graph we might end up with shoes only, bags only, or dress only, but if we define the criteria better (this our teaching lesson) we end up with the top dressed man/women in the world.

Grouping was done by using a spectral clustering algorithm; embedding was done by solving the following problem:

$$\min_{x} \sum_{ij} (\|xi - xj\|2 - d_{ij})2$$

The second objective was to modify the subgraph criteria. This refers to the small molecule: a subgraph is just a way to simplify a molecule in an object that is simple to run with an algorithm, and to easily recall the molecule, or class of molecules, is derived from. (Watch, shoes beg, dress or watch only), making it less restrictive; instead of looking at all the pairs of atoms look only at the close neighbors. Maximum clique based algorithm does not work at this point.

The third objective was to split the data set into two groups based on similarity to a given two molecules and then to split each group further into subgroups based on molecules mutual similarities in each group.

The fourth objective was to find patterns in molecules localized in space and specific locations (such as presence of N-C-N pattern). When looking for similarities between molecules this localization was imposed as an additional constraint. Subgraphs were developed based on distance threshold, maximum connected components and nearest atom idea, The algorithm was then optimized by finding a pattern that optimizes a certain function:

$$\min_{s,|s|=k} E(s) + R(s)$$

Thereafter, a two stage Tabu search was performed to find a pattern minimizing E(s); within proximity of found pattern find a pattern that minimizes R(s); weight differently atoms of different element types; expand resulting subgraphs few steps along the connections. Step 1 consisted of picking few nearest atoms and connect with shortest paths. Step 2 consisted of running a stage 1 Tabu search. The final step consisted of running a stage 2 Tabu search.

The algorithm was further optimized by Machine learning. The problem of Machine learning can generally be formulated as follows: given a set of objects X, a set of labels Y and an objective function:

$$y^*:X \to Y;$$

that maps objects from X to labels from Y; values $y_i=y^*(x_i)$ are known for the limited subset of objects $$\{x_1, \ldots, x_J\} \subset X;$$

called training set; the task is based on the training set to construct an algorithm a: X→Y satisfying: an algorithm should allow efficient computational implementation and the algorithm should be able to correctly reconstruct labels on the training set: $a(x_i)=y_i$, i=1, . . . , J. The equality can be approximate, and the algorithm should have a generalization ability, meaning it should be able to identify with a high accuracy labels on the elements from X that do not belong to the training set (the elements that algorithm has not "seen" before).

This machine learning algorithm was applied to a molecular interaction problem. Here each object is a pair of molecules and each label is a binary value, indicating whether given two molecules interact with each other. The set X is therefore a set of all pairs of molecules, and the set Y contains information on whether molecules from each particular pair interact with each other or not. The training set is essentially data for which the answers are known: a set of pairs of molecules, for which it is known, whether they interact or not. The objective is to design an algorithm, which by learning from the training set, was able to apply obtained knowledge to identify with a high accuracy whether any arbitrary pair of molecules would interact. The following items were crucial in order to successfully solve the machine learning problem: 1) a good training set. A clean high quality set of molecules, for which we are confident in the correct answers. Usually, the larger the training set is, the better is the resulting algorithm, since there is more information for it to learn from. 2) a good representation of objects, which in this case are molecules. The naïve straightforward representations (such as encoding each molecule as a sequence of its atoms with coordinates for each atom) usually don't work. A set of insightful features must be identified from which the algorithm would be able to efficiently learn. 3) finally, in order to test and compare the algorithm, a small testing set of molecules for which there is known answers but which will not be part of the training set is needed. The algorithm was run on this test data set and then the predictions were compared to the known answers. The algorithm has the possibility to enter the process of machine learning if it is provided with a statistical series of data to train the algorithm in advance. If yes, the algorithm uses a machine learning process, if not algorithm can give an immediate answer based on instructions.

The algorithm was used to classify receptors based on a kinase DFG domain pattern. Three different DFG patterns classes were identified: in, out and intermediate (inter).

Handling dual conformations. The DFG motif as discovered in PDB: 1ATP exists in two major conformations IN and OUT. The IN conformation IN kinase is active and sends signals to the network, in the OUT conformation the kinase is inactive and does not send the signal to the network. Identification of INTER using our algorithm and machine learning process is the single most significant accomplishment of this methodology leading to a novel way of designing a small molecules oncology drug.

DFG classification geometrical features for machine learning were identified. Generalized additive models were used:

$$\log\frac{\mu(X)}{1-\mu(X)} = \alpha + s_1(X_1) + \ldots + s_m(X_m)_1$$

$\mu(X) = P(Y=1|X)$
$Y \in \{0,1\}$ is a class;
$X = (X_1, \ldots, X_m)$ are the features
$S_i$ is a nonlinear functions associated with the i-th feature
$\alpha$ is a free term Estimations of risk functions for continuous features function $s_i(x)$ are estimated by fitting natural cubic splines (piecewise polynomial functions):

$$\mathrm{minRSS}(f, \lambda) = \sum_{i=1}^{n}(y_i(x_i))^2 + \lambda \int f''(t)dt;$$

the degrees of freedom (complexity) of the splines are learned in the training process by maximizing the restricted likelihood function; all computations ere done using R mgcv package. Fitting additive models was performed using the following:

Algorithm 9.1 The Backfitting Algorithm for Additive Models.

1. Initialize $\hat{\alpha} = \frac{1}{N}\sum_{1}^{N} y_i, \hat{f}_j \equiv 0, \forall\, i, j$.

2. Cycle: $j = 1, 2, \ldots, p, \ldots, 1, 2, \ldots, p, \ldots,$ $$\hat{f}_j \leftarrow S_j\left[\left\{y_i - \hat{\alpha} - \sum_{k \neq j}\hat{f}_k(x_{ik})\right\}_1^N\right],$$

$$\hat{f}_j \leftarrow \hat{f}_j - \frac{1}{N}\sum_{i=1}^{N}\hat{f}_j(x_{ij}).$$

until the functions $\hat{f}_j$ change less than a prespecified threshold.

The data, shown in Table 1, demonstrated that the algorithm identified 381 molecules in the DFG in conformation, 31 molecules in the DFG out conformation and 44 in DFG intermediate conformations.

TABLE 1

| | |
|---|---|
| Total # of molecules | 467 |
| IN conformation | 381 (82%) |
| OUT conformation | 31 (7%) |
| Intermediate conformation | 55 (11%) |
| # of variables | 30 |

Variable selection. Greedy iterative Forward selection based on 70/30 cross-validation analyses; random split into 70% training subset and 30% testing subset; pick the configuration that gives maximum average ROC over a large number (100-1000) random splits.

Merck data: several approaches were attempted: Simple feature selection (e.g., picking top 100 features with maximal correlation, top 100 features maximal variance, etc.), random forest and GAM models. The variable selection did not improve the results compared to random forest. The results with the top 200 variables sorted by correlation are nearly the same as the results when using an entire dataset.

The final results on DFG pattern classification were as follows: Classification of out versus in, inter: ROC=1; classification of in versus inter: ROC=0.991 for example, the threshold 0.5 corresponds to sensitivity=0.96 and specificity=0.98. The threshold 0.2 corresponds to sensitivity=0.99 and specificity=0.995. Classification of activating versus the rest: ROC=0.88. Classification of resistant mutations versus the rest: ROC=0.71.

Analysis of the pocket of the DFG domain was performed. All ligands in the dataset (1900 molecules) were divided into groups of isomorphic molecules. For each receptor in the dataset (1900 receptors), drug molecules and groups if isomorphic drug molecules that physically fit into the receptor's pocket were determined. The shape of a pocket depends on the drug currently binding to it, so if a drug does not fit into the pocket in its current shape, it does not necessarily mean that the drug cannot fit there in general.

Bias and variance. This represents the way that the algorithm is able to provide the answer to the problem providing statistics and errors distribution. That can be modified to leave the criteria open.

The expected error of a classification (regression) algorithm comes from two sources: 1) Bias the difference between the true value and expected algorithm prediction and 2) variance within the algorithm prediction value:

$$\mathrm{Err}(x)=E(Y-f(x))^2=E(Y-\hat{f}(x)+\hat{f}(x)-f(x))^2=E(Y-\hat{f}(x))^2+E(f(x)-\hat{f}(x))^2=\mathrm{Bias}^2+\mathrm{Variance}$$

Bagging is a way to reduce the variance by averaging a large number of identical algorithms trained on random subsets of data (example Random forest). Boosting is a way to reduce both by averaging a number of adaptively trained algorithms on different sets of data, such that each next algorithm improves on the objects were previous ones made mistakes (example: AdaBoost). Random forest is simply Bagging applied to the random uncorrelated Decision Trees algorithms. A set of trees are trained on random subsets of data and variables the averaged result from all trees is the final result of a Random Forest algorithm. As an example, generalized Boosting Models is Boosting applied to the Decision Tree algorithm. Decision trees have several properties 1) relatively fast to construct and produce interpretable models; 2) naturally incorporate mixtures of numeric and categorical predictor variables and missing values; 3) invariant under (strictly monotome) transformations of the individual predictors; 4) immune to the effects of predictor outliers; 5) perform internal feature selection as an integral part of the procedure; and 6) resistant, if not completely immune, to the inclusion of many irrelevant predictor variables. Results of the receptor pocket analysis were: for the receptor classification problem trained the Random Forest algorithm, received specificity=0.95, sensitivity=0.95. The algorithm out much less weight on individual variables (particularly phosphorylation) and correctly reclassified some of the molecules.

Ligand splitting fragmentation analysis. Splitting the drug molecule and surrounding receptor pocket into distinct functional parts. Spectral clustering algorithm was used in order to split the drug molecules into fragments. The drug molecule graph was used as a similarity graph for the algorithm. We specifically create this task of the algorithm. Any ligand can be divided in small parts until we arrive to a single atom. Similarly, the receptor-binding site can be divided in fragments that interact with the ligand until we arrive to a single atom. Using that option we are able to simplify both the ligand and the receptor into functional parts related to the interactions between ligand and receptor. Through those well-defined parts we are "screening" and we are looking for similarity. It is a similar concept to fragment screening (used routinely in some pharmaceutical companies at significant cost and over a long time to obtain the tangible results. Our process occurs in seconds of machine time, hence reducing the cost to zero.

Example III

Identification of Novel Resistance Mutation in Breast Cancer

Full exon analysis was performed on two patients diagnosed with ER+ breast cancer and who have developed resistance to aromatase inhibitors. Crystallographic analysis of 22,000 gene panels sequenced identified a specific mutation in the tumor cells of both patients that is not present in either patients germ line. Patient #1 exhibited a SNP heterologous mutation in the tumor cell in receptor ESR1, Y537S. Patient #2 exhibited a specific isoform of ESR2 receptor with a SNP heterologous mutation, V497M. Further analysis of the ESR1 mutation adjacent to the residue Y537 demonstrated that the sequence clearly identifies the tyrosine kinase phosphorylation site. Any mutation of tyrosine to serine would therefore result in the loss of control of phosphorylation by both the tyrosine and serine kinases. The only possible phosphorylation event that could occur would be the phosphorylation by the dual specificity kinase MEK. The total loss of phosphorylation controls for Patient #2 can be attributed to the deletion of that identical sequence fragment.

The mutations and deletions identified in both patient #1 and #2 suggest that this phosphorylation site plays a critical role in controlling action of ESR1 and ESR2 and therefore forecasts the complete loss of those controlling functions as the resistance to the aromatase inhibitor grows. Both receptors are constitutively active. It was proposed that signaling continues for patient #1 through the MEK kinase and for patient #2 the signal continues through the mutated PIK3CA. Additionally, besides the mutation in ESR2 and the deletion in ESR2, mutation H1047R and in the PIK3CA were identified. Both of these events can result in overriding the effects of initial therapy because ESR1 and ESR2 act Independently on the estrogen receptor and can activate a cancer driven pathway through either the MEK or through the mutated PIK3CA.

A genetic probe was developed that is designed to specifically monitor the presence or absence of the aforementioned segment, 15 amino acids long, to enable an accurate monitoring methodology to detect the earliest signs of a cascading resistance to the aromatase therapy for breast cancer patients that are ER (+). The probe of that specific segment enables the identification of any single point mutation within the length of the sequence. The probe is targeted to Chromosome 6 for the ESR1 receptor and Chromosome 14 for the ESR2 receptor.

The monitoring aspects of the probe require a blood or saliva sample and a sample of the tumor. The difference found between the blood/saliva and the tumor sample is the critical data set. If the probe does not read the sequence of 15 amino acids in the ESR2 receptor sequence located in the chromosome 14, it will mean that the resistance to the aromatase inhibitor is growing and a new therapy should be Initiated, Similarly for the ESRI receptor in chromosome 6.

Any single point mutation in the region of the ESR1 and ESR2 receptor is an Indication of an increase of activity in the receptor that could develop as resistance to common therapy (Including tamoxifene). The different interpretations can help to identify patients for further therapeutic actions based on the type of the resistance. The goal of this genetic probe is to detect the onset of resistance to existing therapy as early as possible. This monitoring provides a significant advantage over simply observing clinical data of the patient suffering the loss of effectiveness in the aromatase therapy, and falling into relapse.

Example IV

Predication of Patient Resistance to a Therapeutic Agent

The 3D Pattern Matching Machine Learning Algorithm was used to identify a novel mutation in breast cancer patients. Four breast cancer patients had been given prior targeted therapy and had developed resistance to that therapy. Using the algorithm novel actionable mutations were identified and anti-resistance therapies were predicted for the patients. Further, it was discovered that these novel actionable mutations occur in combination with other known oncogenic mutations and a unique combination therapy was proposed. Additionally, the algorithm predicted the functionality of the novel mutation which was confirmed by the predicted solution. Once the algorithm is provided the full functional genome sequencing of a novel mutation, then the process of structural validation starts. Several tasks are run and the algorithm will reach a solution based on different variables (one of them is the critical hydrogen bond network in a specific, selected by trained algorithm, regions. The final answer, after comparing several three dimensional regions, provides the functionality status (activating, resistance or "passenger") and this directs the therapy including the specificity profile run on the proposed inhibitors to minimize the toxicity profile. The target is either specific gene or pathway. Critically, the algorithm also provides a combination of therapy with a combination tox profile (off target).

Example V

Selection of Therapeutic Agents for Specific Mutations

Figure 1B:
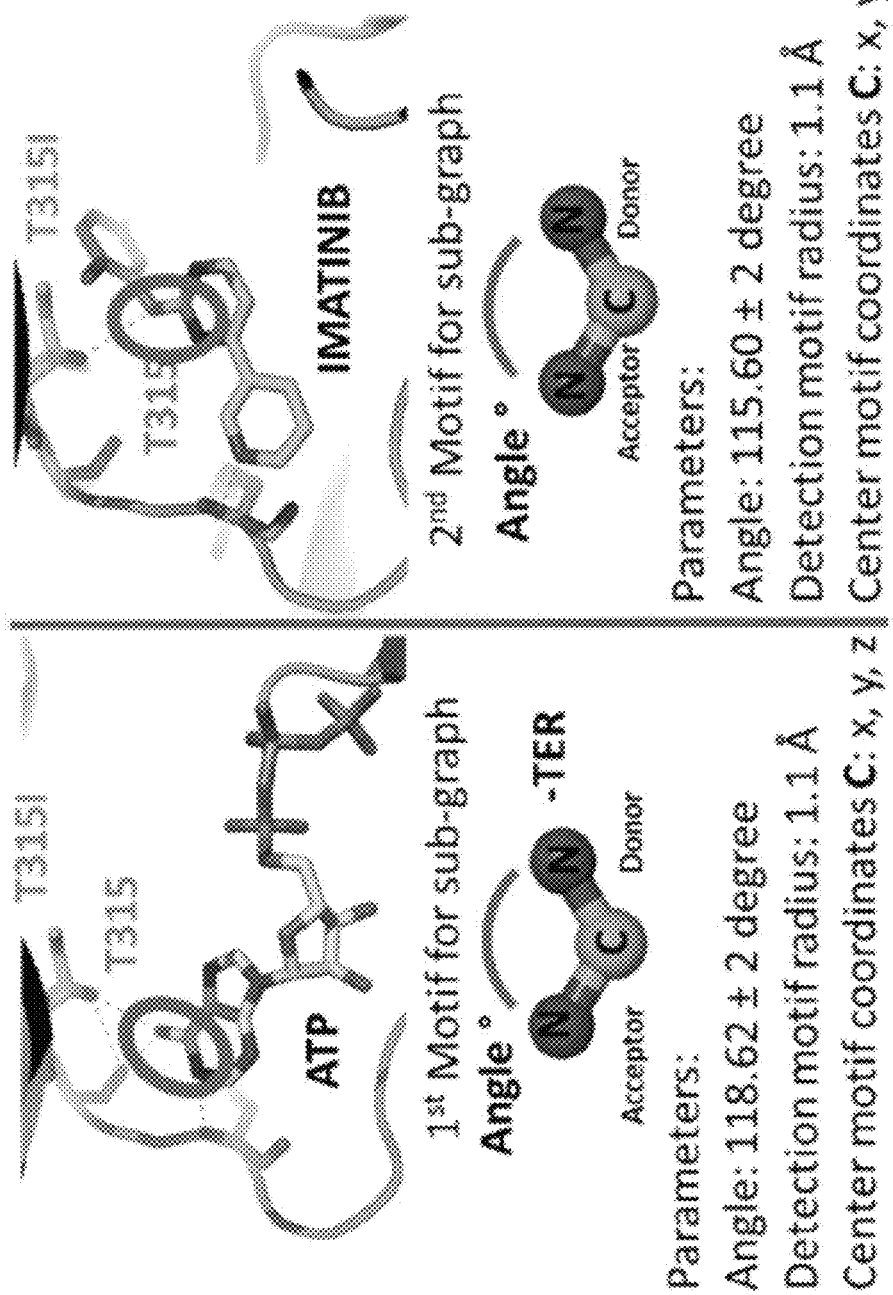
Figure 1C:
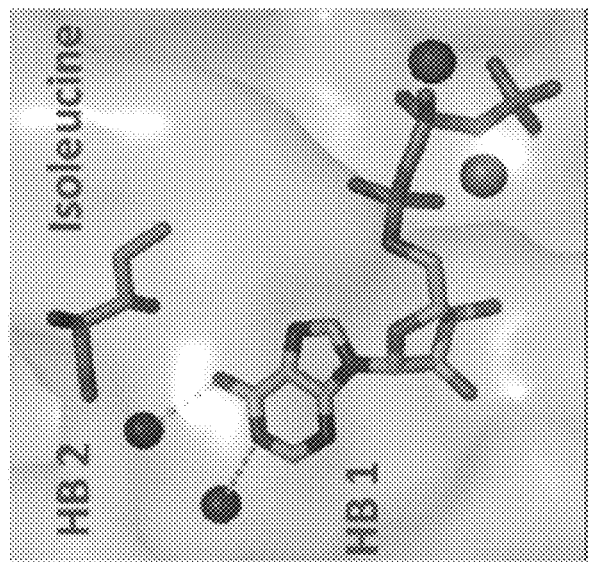
Figure 1C:
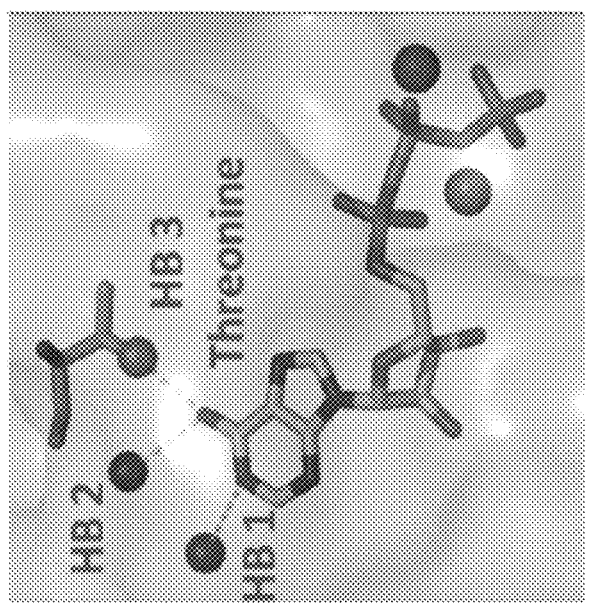
Figure 1D:
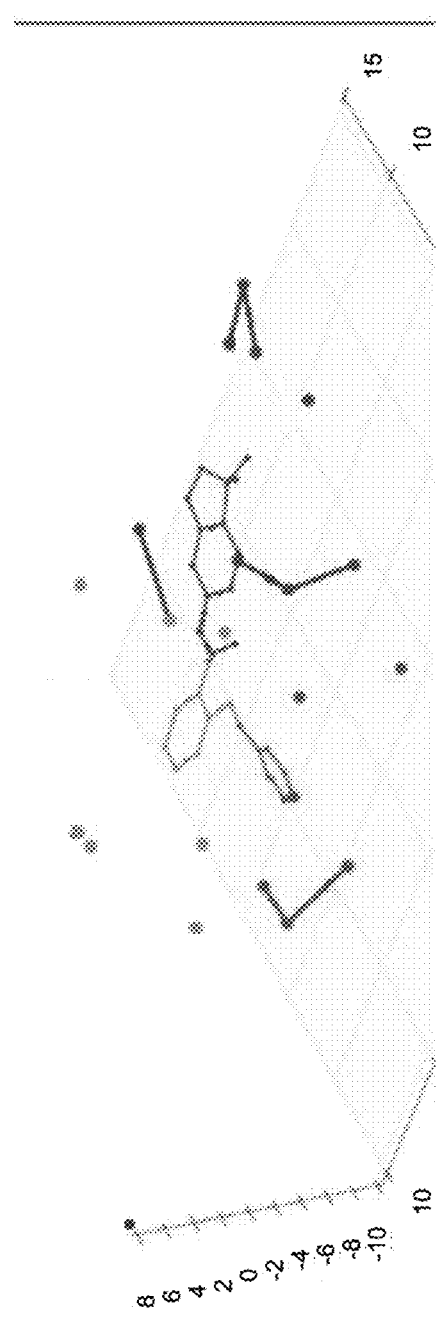
Figure 1E:
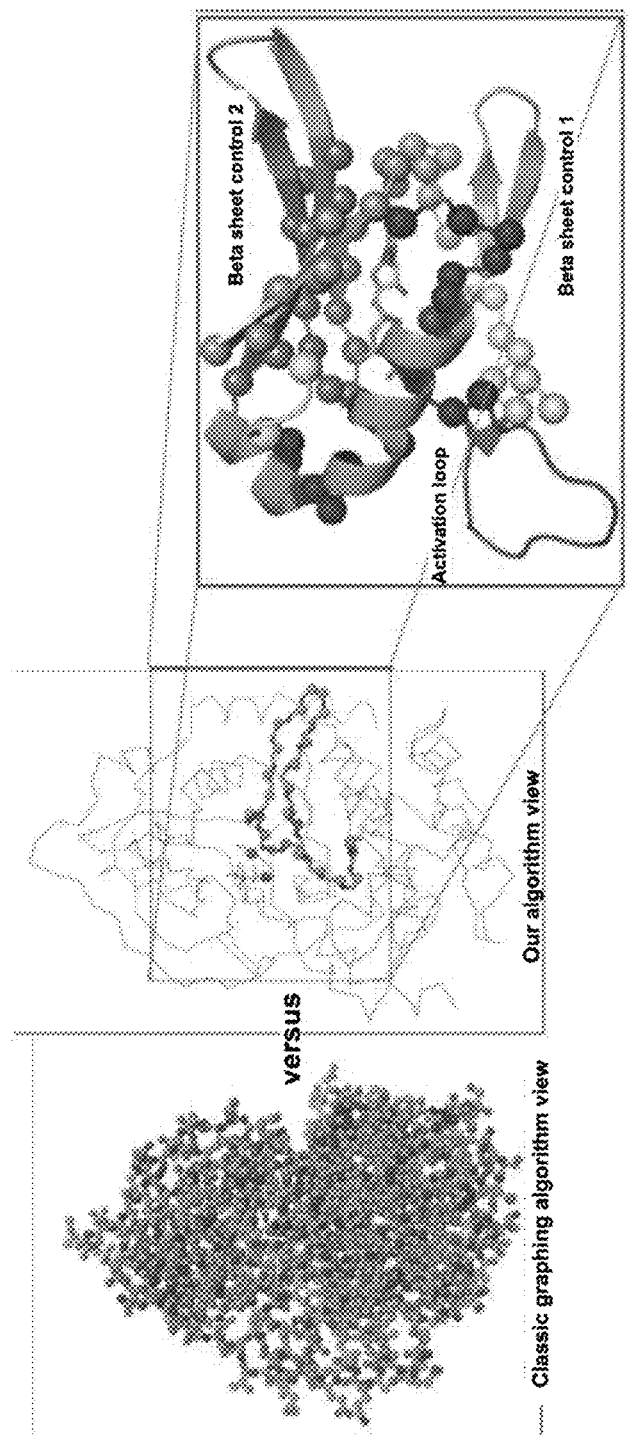

The pattern matching algorithm was used to identify the three dimensional motif of a chemical scaffold and then used for further modifications required for specific genetic makeup of a patient or group pf patients. The algorithm rapidly generated combinatorial modifications to create unique scaffolds (FIG. 1A). The algorithm grouped scaffolds based on their three dimensional structural patterns. The unique and critical pattern of hydrogen bonding of a small molecule (imatinib) to the "linker" between the upper and lower lobe were detected through three dimensional pattern analyses, including the changes of the hydrogen-bonding pattern due to drug resistance (FIGS. 1B and 1C). Each molecule was subdivided in the three dimensional space based on the chemical rules in order to determine the "pocket specificity" (FIG. 1D). The algorithm was taught, using the three dimensional pattern matching, to "walk through" the polypeptide chain toward a specified "specificity pocket" (FIG. 1E) of protein kinase (PKA). Those specificity pockets are very different in the protein kinase DFG motif in conformation (DFG in) vs. the DFG out conformation (DFG out). Using the 3D pattern matching algorithm, it was determined that both activating and resistance mutations create intermediate states with unique specificities. These states were identified using three dimensional pattern matching analysis and a protein kinase crystal structure library. Using a crystal structure database of therapeutic agents binding to the target kinase, specific therapeutic agents were selected to target the unique conformations associated with cancer activating or resistance mutations.

Example VI

Predicting Conformation of Activating and Drug Resistance Mutants

Figure 2A:
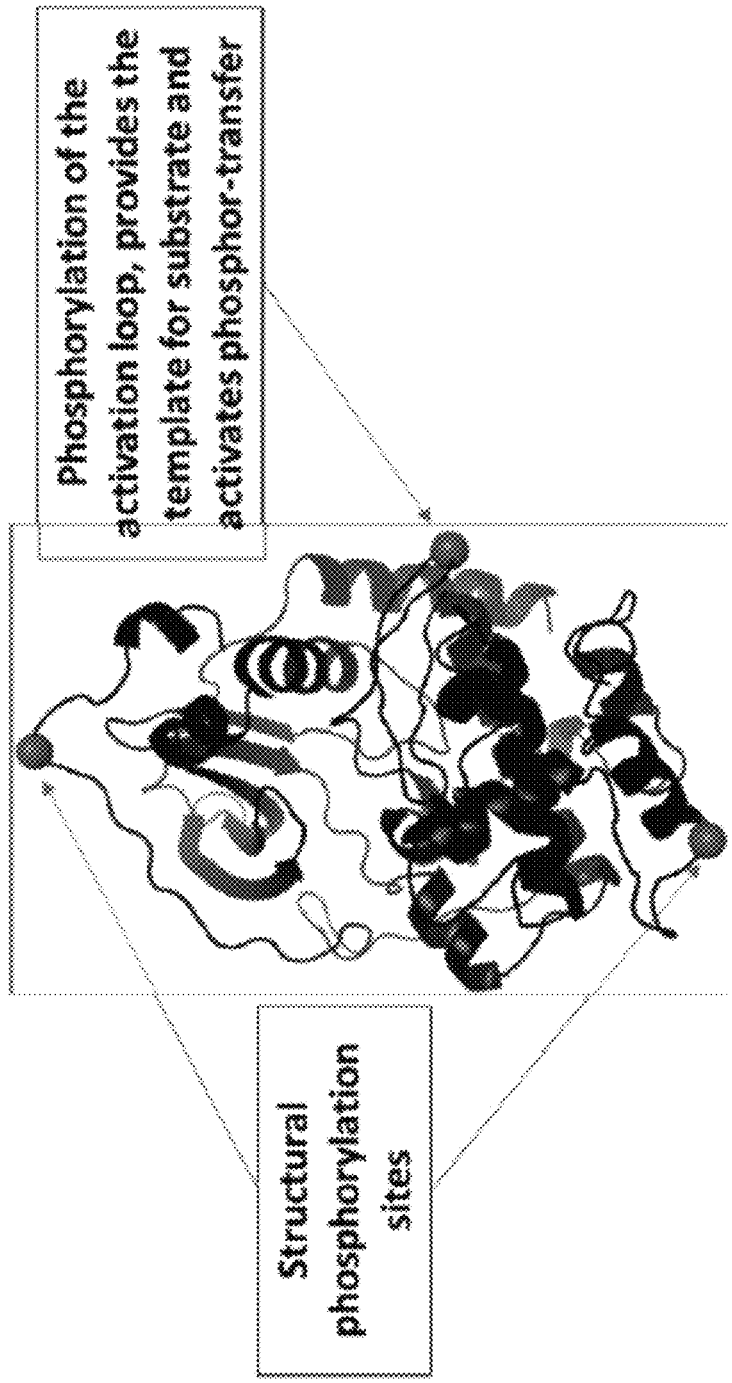
FIGS. 2A-2C show the prediction of kinase domain conformation of a mutation identified from a patient.
Figure 2B:
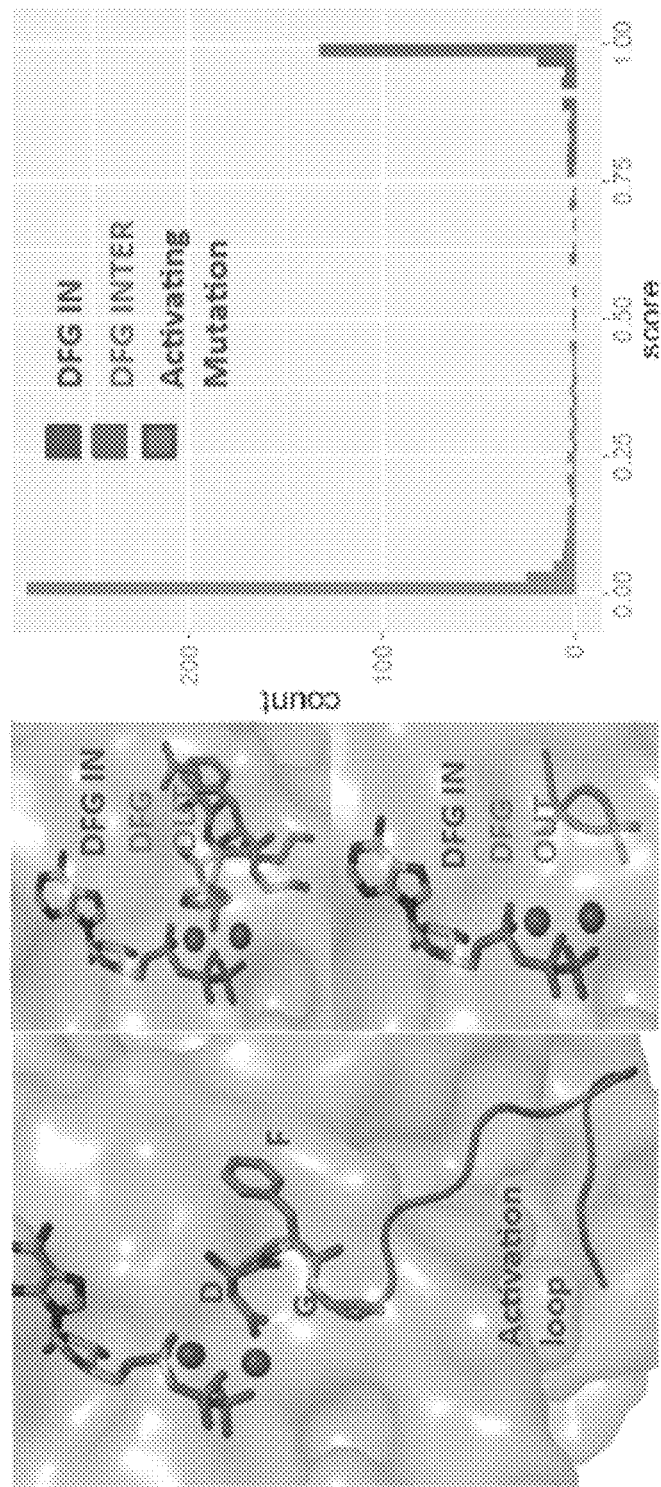
Figure 2C:
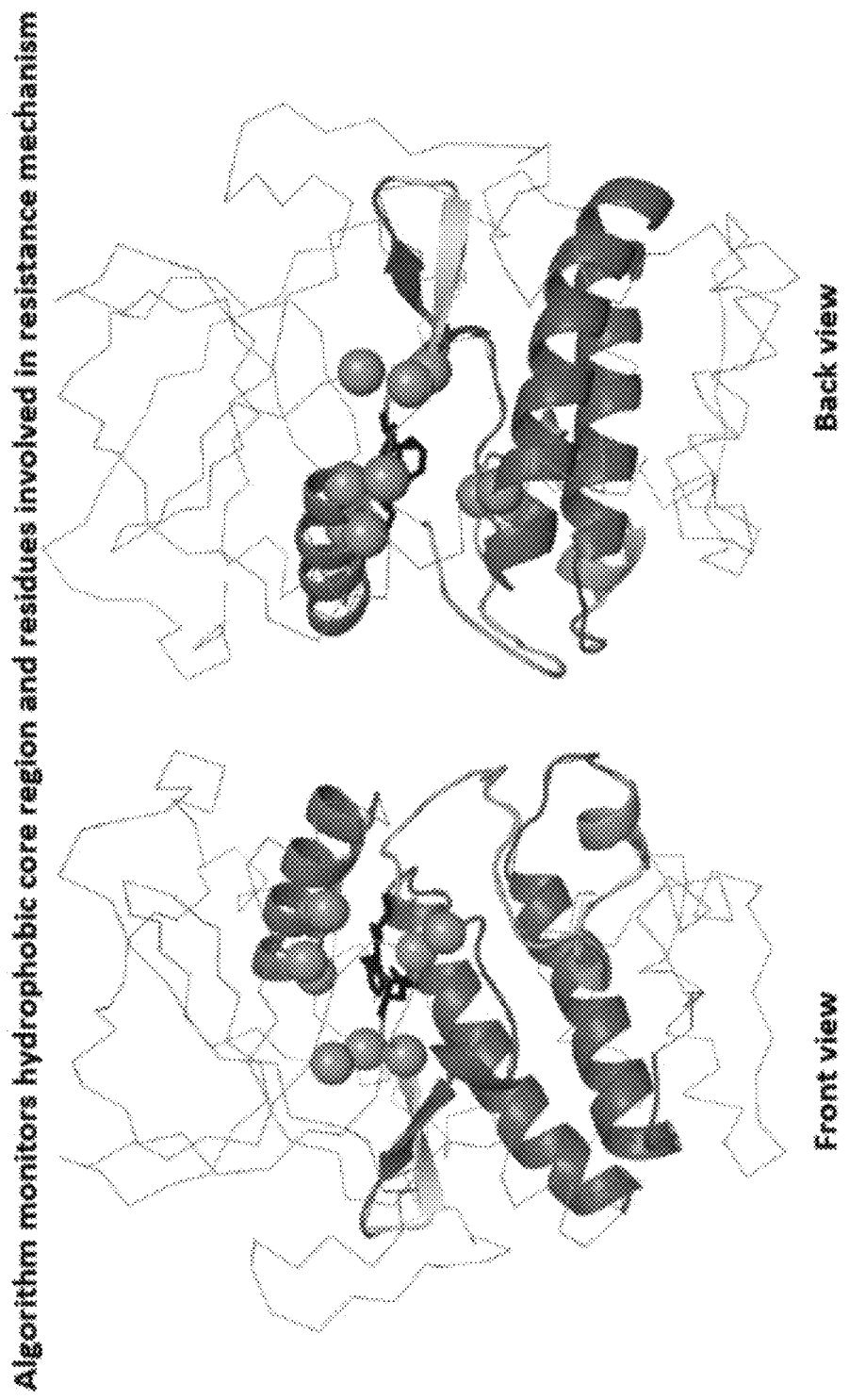

The pattern matching algorithm was used to identify kinase conformation upon phosphorylation and de-phosphorylation. The specificity profile of an inhibitor depends on the conformation of the kinase target. The algorithm recognized the in and out conformation of the DFG motif as well as intermediate conformations (described in previous example). Analysis of one of the intermediate conformations identified one that was associated with activating mutations exclusively positioned on the two pivots of the activation loop and a second group associated with drug resistance mutations forming the hydrophobic core of the most conserved region of the kinase catalytic core. The phosphorylation of the activating loop is a critical part of the activating mechanism of many kinases. The 3D pattern matching algorithm successfully predicted the pattern associated with the phosphorylation of the activation loop (FIG. 2A). Using crystallographic analysis of over 2000 crystal structures, the algorithm predicted the intermediate conformation (FIG. 2B). The hydrophobic network of residues identified by the algorithm and the hydrophobic resistance mutation that keeps the network intact in which neither the in or out DFG conformation is available. The activation mutation, acting on the two pivots of the activating loop, create an intermediate conformation of the DFG motif (FIG. 2C). The specificity profile of the intermediate conformation is neither in nor out creating the template designing small molecules which target the cancer activating or resistance mutation.

Example VII

Predicting the Specificity Profile of Novel Small Molecule Inhibitor

Figures 3C, 3D:
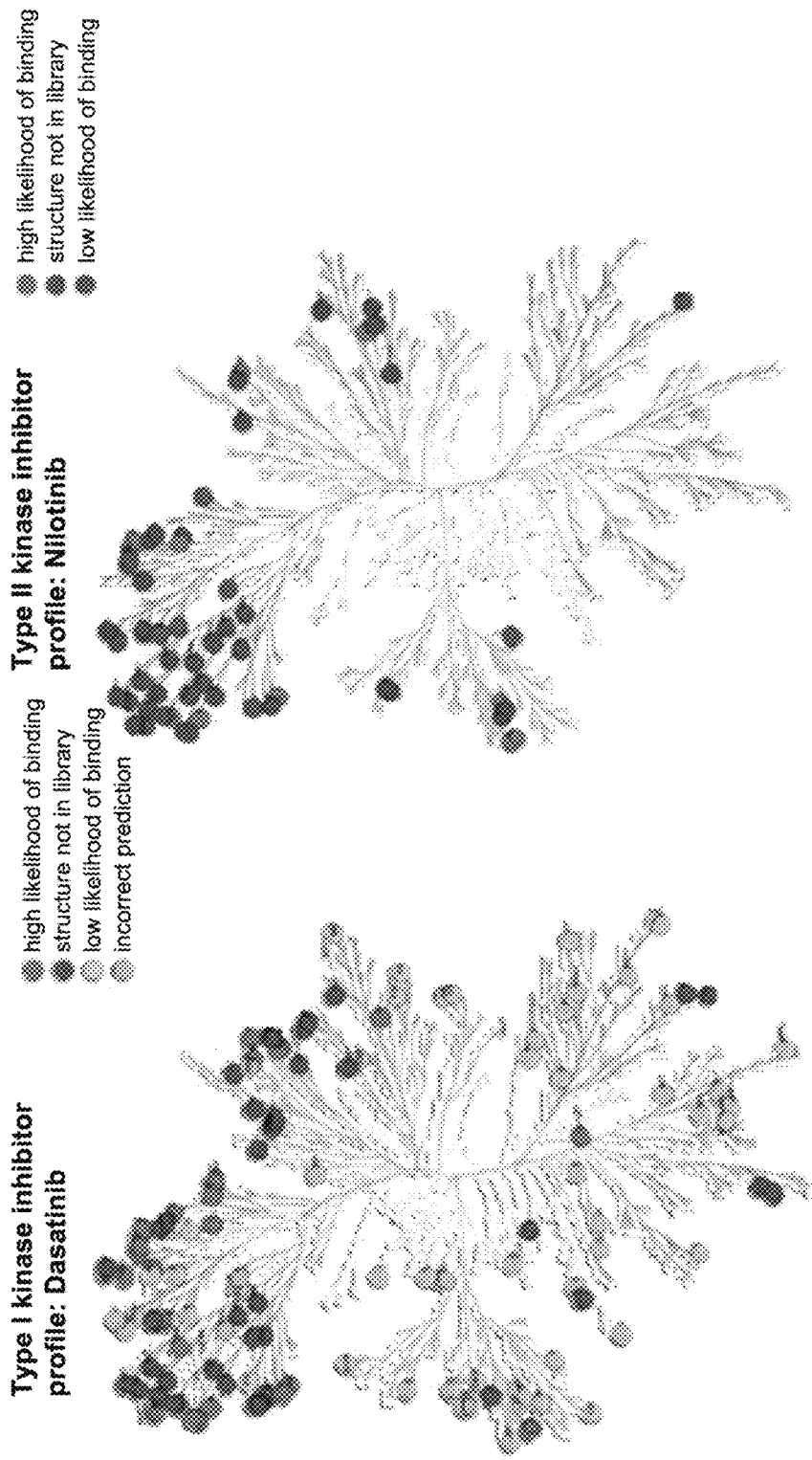
Figure 3E:
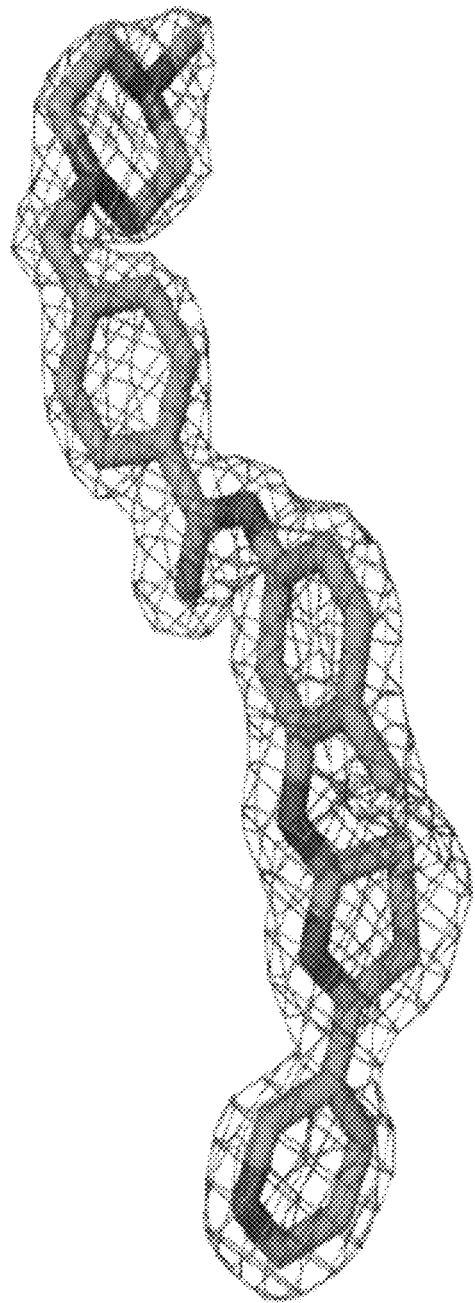
Figure 3F:
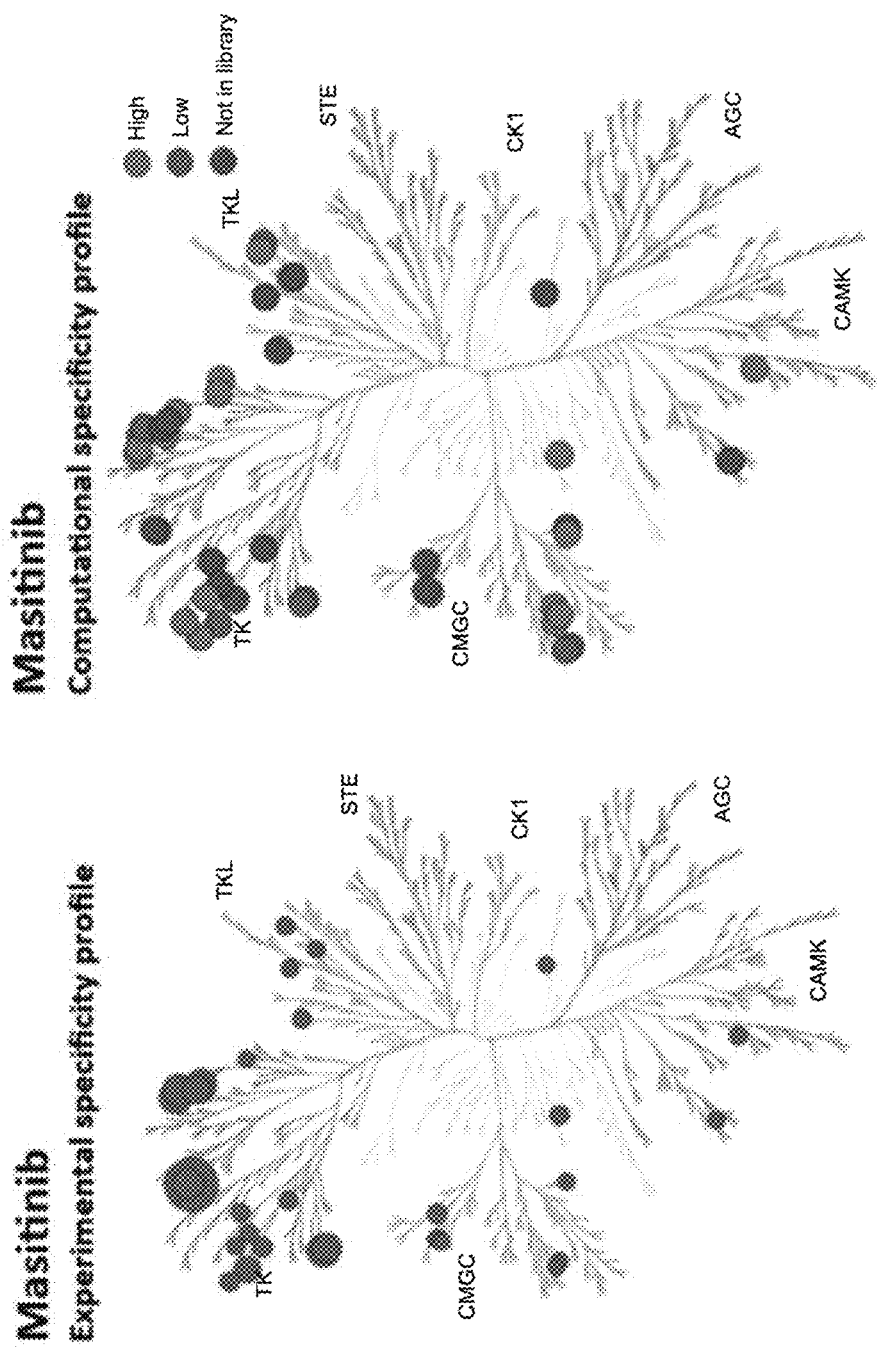

Selection of a scaffold using an algorithm also require selection of specificity profile of the desired scaffold to create a patient molecule or molecules, The need is not simply to define which residues dictate the particular conformational state and which residues do not, but also to define the unique pockets characteristic for the subgroup of the kinases, this grouping is based on the extent of conservation and can be identified the algorithm's use of the intermediate states. Highly conserved forms a unique pattern of interatomic distances across the two flexible lobes—diverse are pointing out to evolutionary diversity of the ATP binding site. The combination of algorithmic analysis creates the unique pattern for each major conformational state. In those intermediate states associated with activating and resistance mutations the algorithm can predict, even for a never co-crystallized molecule, the correct affinities after a successful prediction of profiles for those molecules, which have been co-crystallized. Predicted specificities for dasatinib (binds the DFG in conformation) and nilotinib (binds the DFG out conformation) resulting from the analysis of the crystal structure library using the 3D pattern matching software were compared to published data. The algorithm correctly predicted the specificity profile for nilotinib and only had three incorrect predictions for dasatinib (FIGS. 3C and D). The lower number of targets for nilotinib as compared to dasatinib suggest more "specific DFG out conformation (inactive) than the "less specific" but fully active DFG in conformation. A similar comparison was made for masatinib (FIGS. 3E and F).

Example VIII

Predicting Activating Mutations

Figure 4A:
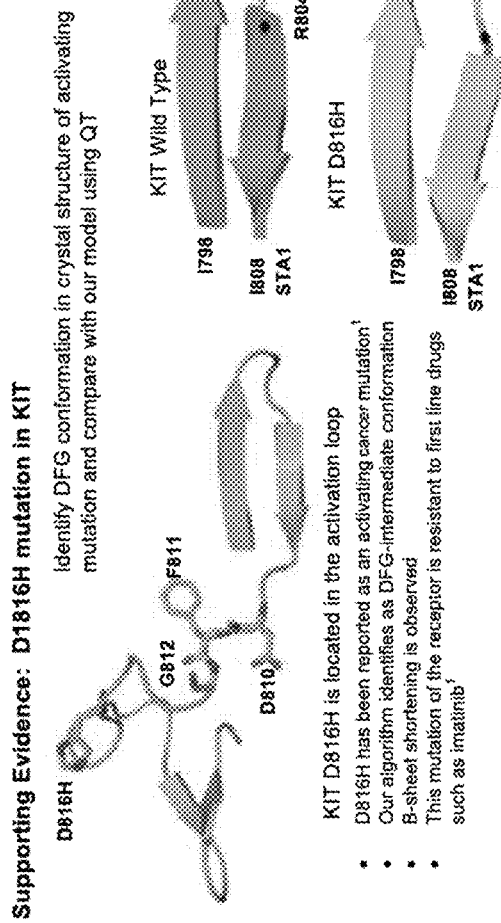
FIGS. 4A-4C show the determination that a kinase mutation is activating.
Figures 4B, 4C:
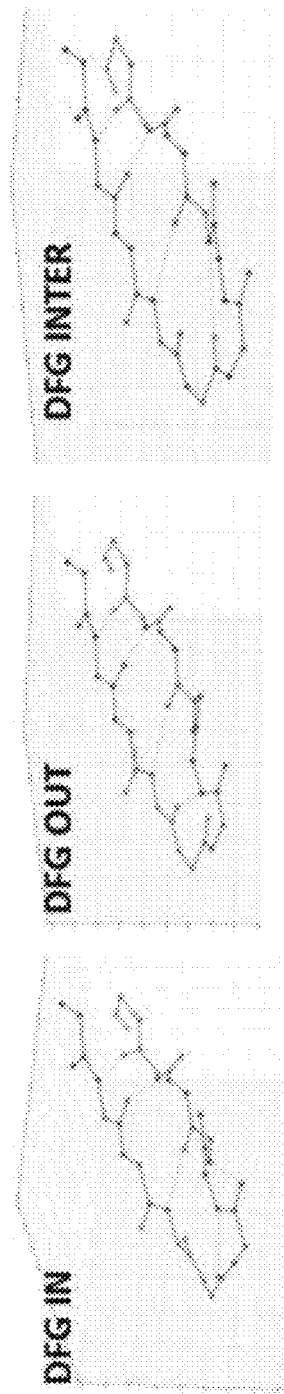
Figure 5:
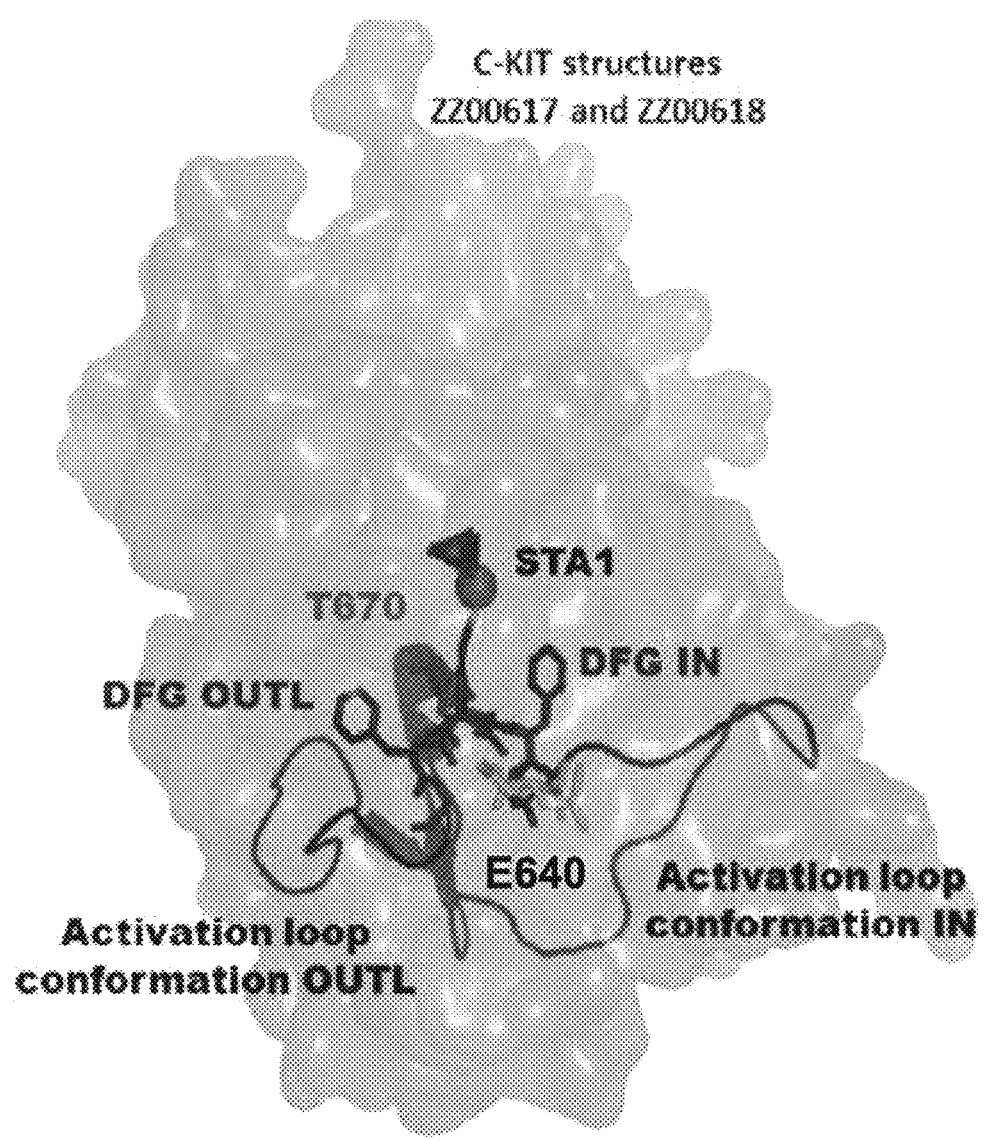
FIG. 5 shows superimposition of C-KIT structures from DNA-SEQ library ZZ00617 (PDB ID 1KPG) and ZZ00618 (PDB ID 1T46). ZZ00617 has DFG in conformation IN and ZZ00618 has DFG in conformation OUTL. Visualized from the top of the kinase. The transparency of the electrostatic surface makes it possible to observe structure details, like STA1, that coincide in both structures, DFG OUTL and DFG IN, the two different conformation of activation loops, the mutant position T670 and conserved position E640.
Figure 6:
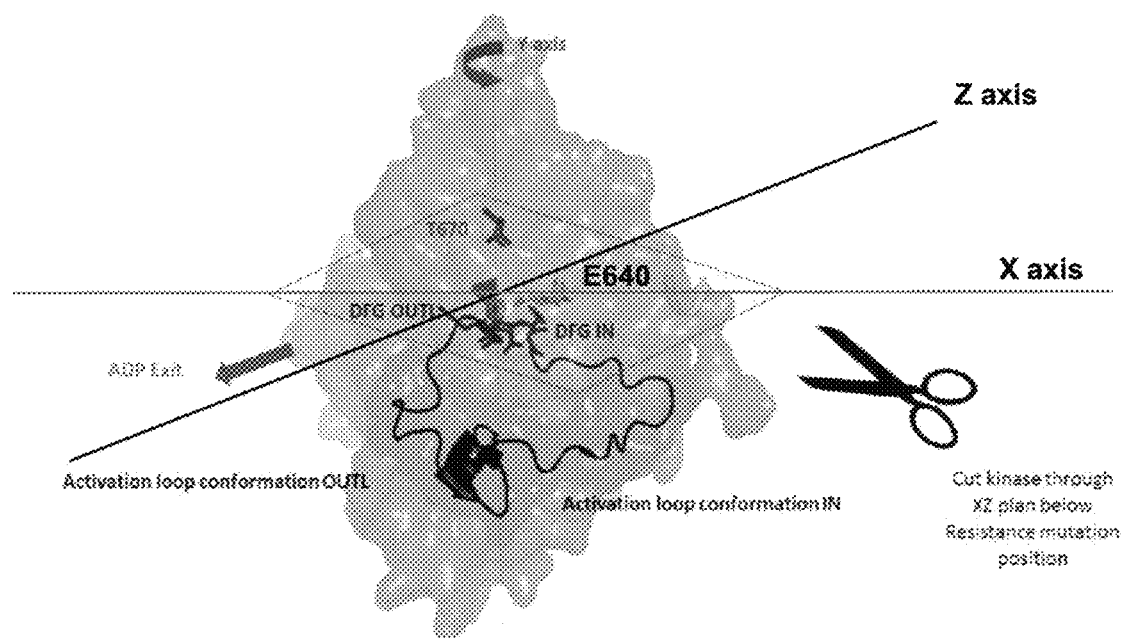
FIG. 6 shows the same structure as FIG. 5 from another perspective. The same details are visualized to identify axis y passing through T670, axis x passing through E640, and axis z passing through ADP exit trajectory.
Figure 7:
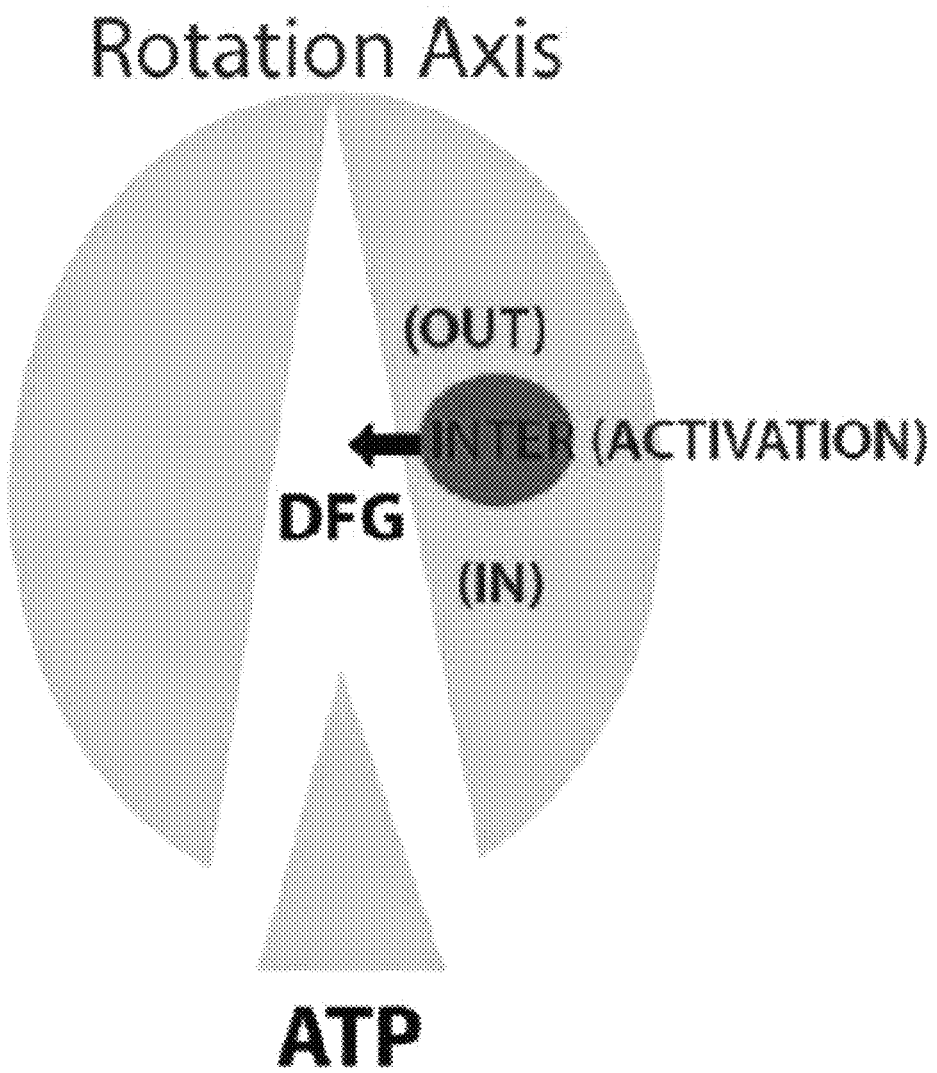
FIG. 7 is a schematic diagram of the bi-lobal homologous catalytic core of a protein kinase, with a two-fold roto-translation axis, and the DGF motif outlined (arrow). The red colored circled indicates the activation loop that is detailed in FIG. 8.
Figure 8:
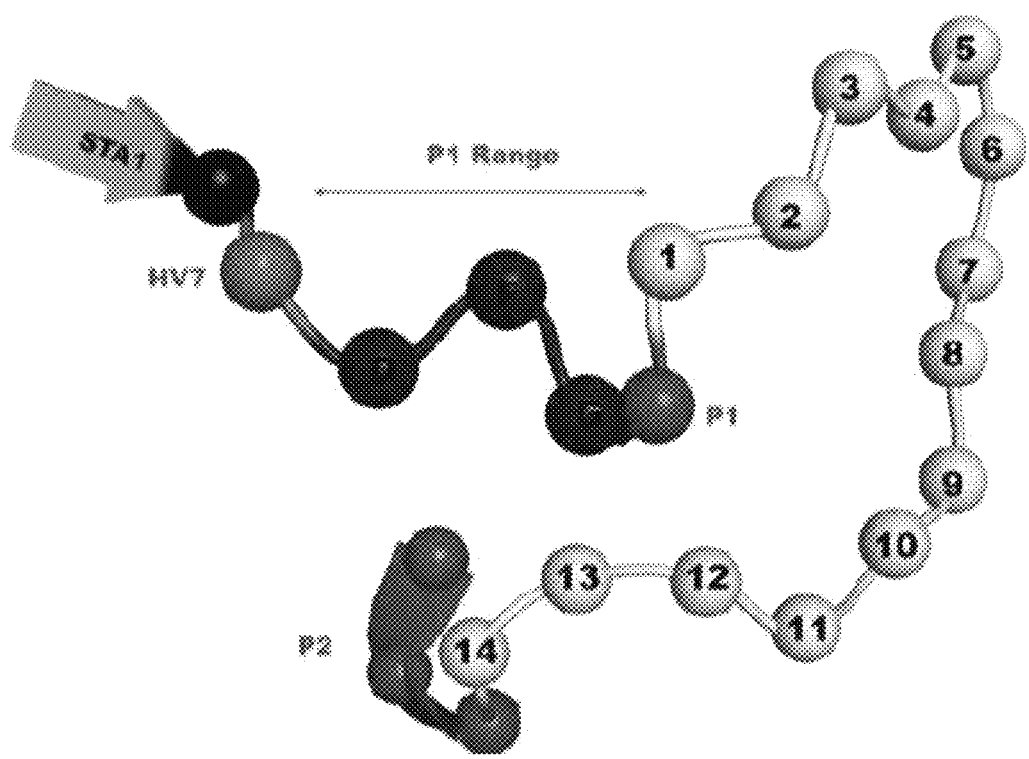
FIG. 8 shows C (alpha) coordinates of the first crystal structure of kinase (PKA pdb id: 1ATP) encompassing DFG motif and activation loop. This part of the catalytic core is firmly embedded in the most conserved part of the core, yet by itself it is highly diverse, except the canonical DFG motif. It is the critical highly flexible part that transmits the activation process (phosphorylation) into enzymatic action (PKA is always active as it is activated by release of regulatory subunit upon cAMP binding). The activation mechanism is diverse among kinases; for example autophosphorylation requires release of inhibitory domain to allow ATP entry. Hence this type of mechanism requires binding of the signaling molecules (hormones, CA (+2) etc.). The STA1 (from a static) position usually has low temperature factors. This is the first hydrophobic residue in the "pivot 1 range". Following that, the residue HV7 is highly variable and forms a critical part of "pivot1". Certain kinases "switch" from the IN to the OUT DFG conformation at that point. Following HV7 is the DFG motif as reported in the previous section it is the highly dynamic motif which binds two metal sites (specifically D). Following DFG motif is the residue P1 (pivot 1). This is the critical highly diverse residue among kinases and it is very rich in cancer "activation" mutations. Based on our pattern matching analysis this residue is responsible for the high conformational diversity of the DFG motif, as previously mentioned. The residues, 1 through 14, represent the highly diverse activation loop. Here the kinase subfamily is highly differentiated and phosphorylation (or auto phosphorylation) can occur at any residue, depending on the kinase or kinase subfamily. P2 ("pivot 2") is a series of three residues in a short alpha helix conformation. At P2 many kinases undergo an IN/OUT conformation change which alters the surrounding structural microenvironment.
Figure 9:
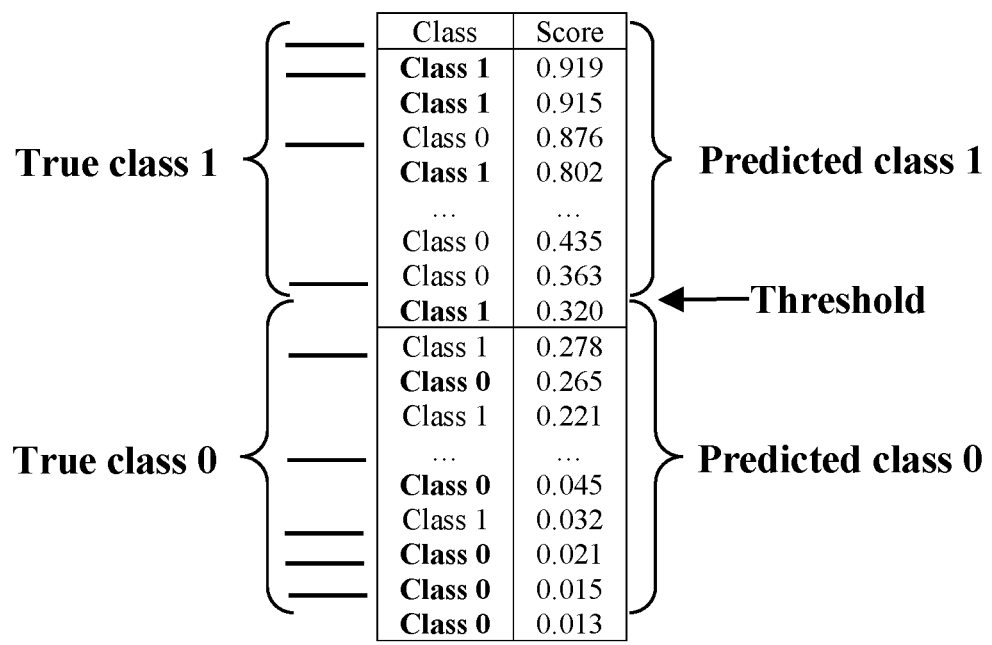
FIG. 9 illustrates the accuracy of the fitting models as described.

The 3D pattern matching algorithm was used to identify an activating mutation of KIT D816H, which is resistant to treatment with imanitib. The algorithm identified the DFG intermediate conformation associated this mutation (FIG. 4A). Imanitib binds only to the DFG out conformation and does not bind this intermediate conformation. This activating mutation results in shortening of the beta strand and the reorganization of the beta strand hydrogen bonding network (FIGS. 4B and C). Since the beta strand lies on the interface between the upper and lower domains of the intermediate conformation of the DFG motif this activating mutation results in changes in the activity of the protein.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding specific embodiments are to be construed as merely illustrative, and not limiting of the scope of the invention in any way whatsoever. The entire disclosure of all applications, patents, publications (including reference manuals) cited above and in the figures, are hereby incorporated in their entirety by reference.

Example IX

Molecular Mechanism of Phosphotransfer and Its Regulation in Certain Kinases

The bridge is a kinetic model of the mechanism of phosphotransfer, as deduced from hundreds of somatic mutations of cancer patients, using the three dimensional pattern matching algorithm and crystal structures library.

The key utilities of this invention emerge from a model that is based on the data of cancer patients.

In essence, the original discovery of the structure of the ternary complex of the catalytic subunit, with Mg ATP and substrate, mimics the specific inhibitor peptide that resulted in the first three dimensional template used for medicinal chemistry to design Gleevec®.

This template was very successful in part due to the homology modeling conducted by using the coordinates of the aforementioned ternary complex. This revealed amino acid diversity at various pockets around the ATP binding site. The success of Gleevec® in clinics resulted in the unprecedented development of kinase inhibitors. Today there are 33 FDA approved drugs.

However, an alarming, unanticipated consequence emerges over time—patient's resistance to the drug. The most prominent resistance site is located at the "linker" connecting two lobes of the enzyme. The "Gate keeper residue" term was coined and numerous publications refer to this site while lacking a clear understanding of what it means in terms of the mechanism of the enzyme.

The forgoing problem was attacked by detailing the molecular mechanism by using hundreds of patients mutants, 7 million unique XYZ kinase coordinates (stored in the crystal structure library), and the proprietary, super fast three dimensional pattern matching algorithm (licensed exclusively from first Commercial Quantum Computer Company D-WAVE).

The final results of the calculations were validated using thermal shift calorimetric (TSA) and surface Plasmon resonance (SPR) as applied to the GIST resistant mutant of ckit T670I.

The corollary of this invention, based on the kinetic model of phosphotransfer, is a departure from the original design strategy of Gleevec®. This design strategy is an evolution in that it is a new three dimensional template that encompasses the pathway wherein cancer "hijacks" the phosphotransfer mechanism in kinases as activated by phosphorylation. In essence, the patient response provides the three dimensional template for drug design. This evolution is made possible through pattern matching technology.

Example X

Hijack Mechanism of Cancer

Over six hundred publications are covered by the kinase somatic mutations library. The mutation selected for further analysis only occurs in the catalytic cores of kinases in cancer patients, and it has been reported in all cancer indications. An aspect of the present invention is the use of the inventors' crystal structures and algorithm, and the results revealed by the crystal structures and algorithm together with the use of biophysical methods. A further significant aspect of the present invention is the three dimensional template for the medicinal chemistry focused design.

The known activating and resistance mutation within the catalytic core are outlined in Table I.

TABLE I

| Drug | Activating Mutations | Resistant Mutations |
| --- | --- | --- |
| Afatinib | EGFR: L858R [1] | EGFR: T790M [2] |
| Axitinib | No Study Found | No Study Found |
| Bosutinib | BCR/ABL: H396P/R, F359V, Q252H and L384M [3] | BCR/ABL: T3151, V299L (3) |
| cabozantinib | MET Y1248H, D1246N, K1262R [4] | VR04M [3] |
| Ceritinib | No study found | ALK: L1196M, G1269A, L1152R, C1156Y, G1202R, and S1206Y [6] |
| Cetuximab | BRAF: V600E [7] | EGFR: S492R [8] |
| Cobimetinib | Braf: V600 mutation [9] | No Study Found (newer drug) |
| Crizotinib | ALK: I1171N R1275Q [10] | ALK: S1206Y, L1196M, G1202R [11] |
| Dasatinib | BCR/ABL: H396P/R, F359V [3] | BCR/ABL: T315I [3] |
| Erlotinib | EGFR: L858R [12] | T790M [13] |

TABLE I-continued

| Drug | Activating Mutations | Resistant Mutations |
|---|---|---|
| Gefitinib | EGFR: L858R, L861Q [14] | T790M [13] |
| Ibrutinib | BTK: L265P [15] | BTK: C481S |
| | | PLCγ2: S707Y, R665W, and L845F [16] |
| Imatinib | No study found | KIT: T670I |
| | | ABL: T315I [17] |
| Lapatinib | HER2: G309A, D769H, D769Y, V777L, V842I, and R896C [18] | HER2: L755S [18] |
| Lenvatinib | RET: C634W, M918T [19] | No Study Found (newer drug) |
| Nilotinib | BCR/ABL: F317L [3] | BCR/ABL: T315I, E255V [3] |
| Osimertinib | EGFR: T790M [20] | No study found (newer drug) |
| Palbociclib | ER-LBD: Y537S, Y537N and D538G [21] | No Study Found |
| Pazopanib | No Study Found | No Study Found |
| Pegaptanib | No Study Found | No Study Found |
| ponatinib | T315I mutant ABL [22] | BCR-ABL 1T315I/F359V [23] |
| Regorafenib | No Study Found | No Study Found |
| Ruxolitinib | JAK2: V617F [24] | JAK2: V617F [25] |
| Sorafenib | PDGFRA: T674I [26] | FIPILI-PDGFRA: D842V [27] |
| Sunitinib | KIT: L576P [28] | KIT: D816H/V [29] |

The resistance mutations resulting from the action of specific drugs within the catalytic core are outlined in Table II.

TABLE II

| Gene | Mutation | Drug | Finding |
|---|---|---|---|
| ABL1 | T315I | Imatinib | Patients were shown to have the mutation both before and after drug use. [1] |
| EGFR | T790M | Gefetinib/Erlotinib | Mutation acquired via the drugs. Mutation not shown pre-treatment. [2] |
| ERBB2 | T798I | Lapatinib | Not reported to be in a before/after study, but does cause drug resistance. [3] |
| KIT | T670I | imatinib | not found in tumor samples prior to drug testing/found to cause drug resistance. [4] |
| PDGFRA | T674I | imatinib | Multiple papers refer to it as an acquired mutation. This seems widely accepted. [5] |

It is important to refer to clinical data that clearly indicates in some cases, the "resistant" mutation has been present prior to administering the drug. As has been presented in Tables I and II, the specific cancer indications are not listed, but this data is used for interpretation of the clinical results based on the three dimensional network of interactions between the mutated cancer patient target and a specific drug. Perhaps, the most intriguing part of the initial analysis is that the clinical results suggest that patient response can be translated into three-dimensional space (crystallographic analysis with pattern matching algorithm) and that the resulting analysis can be used to discover the intimate mechanism regulating the activity of the patient's kinase target.

The patient's kinase regulatory domain mutants cannot be translated, but, through pattern matching analysis, both the activating and resistance mutations can be correlated with the binding of the drug, and more importantly, how the binding of the ATP competitive inhibitor results in aggressive resistance, and subsequently, how this knowledge can be used for design based on the genomic information of the patient. Here the predictive methodology has been applied to two critical 3D patterns; the very highly conserved DFG motif, and the highly variable linker region. Both have been originally described in the crystal structure of PKA.

Although the disclosure has been described with reference to the above examples, it will be understood that modifications and variations are encompassed within the spirit and scope of the disclosure. Accordingly, the disclosure is limited only by the following claims.

What is claimed is:

1. A method of determining risk for developing resistance or monitoring the further development of resistance to a first therapeutic agent in an ER+ breast cancer patient comprising:
   a) obtaining a biological sample and a tumor sample from the patient;
   b) contacting the biological sample and the tumor sample from the patient with a probe that binds to a region of a sequence in a gene associated with kinase phosphorylation to identify at least one mutation,
   wherein binding of the probe with the biological sample but not the tumor sample is indicative of a tumor that is at risk for developing resistance to a therapeutic agent;
   c) using a pattern matching algorithm to determine if the at least one mutation is an activation mutation or a resistance mutation; and
   d) using the pattern matching algorithm and a crystal structure library to identify therapeutic agents to target the activation mutation or resistance mutation, thereby identifying the risk for developing resistance or monitoring the further development of resistance to the first therapeutic agent optionally administering the first therapeutic agent to the patient and optionally repeating steps a) and b) at different time points in the patient's treatment.

2. The method of claim 1, wherein the mutation is a deletion or a point mutation.

3. The method of claim 1, wherein the gene sequence is an ESR1 or ESR2 receptor gene sequence.

4. The method of claim 3, wherein the ESR1 receptor has a point mutation at Y537, E380, L536 or D538.

5. The method of claim 4, wherein the point mutation is Y537S, Y537A, Y537E or Y537K.

6. The method of claim 3, wherein the ESR2 receptor has a point mutation at V497.

7. The method of claim 6, wherein the point mutation is V497M.

8. The method of claim 1, wherein the first therapeutic agent is selected from the group consisting of an aromatase inhibitor, tamoxifen, Raloxifene and a competitor of estrogen in its ER binding site.

9. The method of claim 1, further comprising predicting a response to a second therapeutic agent.

10. The method of claim 9, wherein the first therapeutic agent is an aromatase inhibitor and the second therapeutic agent is a non-aromatase inhibitor chemotherapeutic drug.

11. The method of claim 1, wherein the biological sample is selected from the group consisting of a blood, saliva, urine, bone marrow, serum, lymph, cerebrospinal fluid, sputum, stool, organ tissue and ejaculate sample.

* * * * *